United States Patent
Peterson et al.

(10) Patent No.: US 10,463,512 B2
(45) Date of Patent: *Nov. 5, 2019

(54) APPARATUS AND METHODS FOR FILLING A DRUG ELUTING MEDICAL DEVICE VIA CAPILLARY ACTION

(71) Applicant: Medtronic Vascular, Inc., Santa Rosa, CA (US)

(72) Inventors: Justin Peterson, Santa Rosa, CA (US); James Mitchell, Windsor, CA (US); Abby S Pandya, Boston, MA (US); Nate Glucklich, Santa Rosa, CA (US); Joseph Berglund, Santa Rosa, CA (US); Ya Guo, Irvine, CA (US)

(73) Assignee: Medtronic Vascular, Inc., San Rosa, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 15/376,398

(22) Filed: Dec. 12, 2016

(65) Prior Publication Data
US 2017/0086996 A1 Mar. 30, 2017

Related U.S. Application Data

(63) Continuation of application No. 13/457,398, filed on Apr. 26, 2012, now Pat. No. 9,549,832.

(51) Int. Cl.
*A61F 2/91* (2013.01)
*A61L 31/16* (2006.01)
*A61F 2/82* (2013.01)

(52) U.S. Cl.
CPC .................. *A61F 2/91* (2013.01); *A61F 2/82* (2013.01); *A61L 31/16* (2013.01);
(Continued)

(58) Field of Classification Search
CPC .......... A61F 2/82; A61F 2/91; A61F 2240/00; A61L 2420/02
See application file for complete search history.

(56) References Cited

U.S. PATENT DOCUMENTS 4,886,062 A 12/1989 Wiktor
5,019,090 A 5/1991 Pinchuk
(Continued)

FOREIGN PATENT DOCUMENTS

| WO | WO2004091686 | 10/2004 |
| WO | WO2011008896 | 1/2011 |
| WO | WO2012036929 | 3/2012 |

OTHER PUBLICATIONS

JP 2015-508939, 1st Japanese Office Action, dated Nov. 25, 2016.
(Continued)

*Primary Examiner* — Andrew D Stclair
(74) *Attorney, Agent, or Firm* — Medler Ferro Woodhouse & Mills PLLC

(57) ABSTRACT

Methods and apparatus are disclosed for filling a therapeutic substance or drug within a hollow wire that forms a stent. The stent is placed within a chamber housing a fluid drug formulation. During filling, the chamber is maintained at or near the vapor-liquid equilibrium of the solvent of the fluid drug formulation. To fill the stent, a portion of the stent is placed into contact with the fluid drug formulation until a lumenal space defined by the hollow wire is filled with the fluid drug formulation via capillary action. After filling is complete, the stent is retracted such that the stent is no longer in contact with the fluid drug formulation. The solvent vapor pressure within the chamber is reduced to evaporate a solvent of the fluid drug formulation. A wicking means may control transfer of the fluid drug formulation into the stent.

16 Claims, 29 Drawing Sheets

(52) U.S. Cl.
CPC ... *A61F 2240/00* (2013.01); *A61F 2250/0068* (2013.01); *A61L 2420/02* (2013.01)

(56) References Cited

U.S. PATENT DOCUMENTS

| | | | |
|---|---|---|---|
| 5,133,732 | A | 7/1992 | Wiktor |
| 5,782,903 | A | 7/1998 | Wiktor |
| 6,136,023 | A | 10/2000 | Boyle |
| 6,743,462 | B1 * | 6/2004 | Pacetti ............... A61L 31/10 427/2.24 |
| 7,563,324 | B1 | 7/2009 | Chen et al. |
| 7,901,726 | B2 | 3/2011 | McMorrow et al. |
| 8,291,854 | B2 | 10/2012 | Behnisch et al. |
| 2003/0104030 | A1 | 6/2003 | Igaki et al. |
| 2004/0200729 | A1 | 10/2004 | Boulais et al. |
| 2008/0233267 | A1 | 9/2008 | Berglund |
| 2009/0035351 | A1 | 2/2009 | Berglund et al. |
| 2009/0143855 | A1 | 6/2009 | Weber et al. |
| 2011/0008405 | A1 | 1/2011 | Birdsall et al. |
| 2011/0034992 | A1 * | 2/2011 | Papp ..................... B05D 1/002 623/1.16 |
| 2011/0070357 | A1 * | 3/2011 | Mitchell ................ A61L 31/16 427/2.25 |
| 2011/0264187 | A1 | 10/2011 | Melder |
| 2012/0067008 | A1 | 3/2012 | Bienvenu |
| 2012/0067454 | A1 | 3/2012 | Melder |
| 2012/0070562 | A1 | 3/2012 | Avelar et al. |
| 2012/0216907 | A1 | 8/2012 | Pacetti |

OTHER PUBLICATIONS

Kim et al. "Electrically Controlled Hydrophobicity in a Surface Modified Nanoporous Carbon" Applied Physics Letters 98, 053106 (2011).

Vallet et al. "Electrowetting of Water and Aqueous Solutions on Poly(ethylene Terephthalate) Insulating Films" Polymer vol. 37, No. 12, pp. 2465-2470, 1996.

U.S. Appl. No. 61/244,049, filed Sep. 20, 2009, Thompson et al.

U.S. Appl. No. 61/244,050, filed Sep. 20, 2009, Silver et al.

* cited by examiner

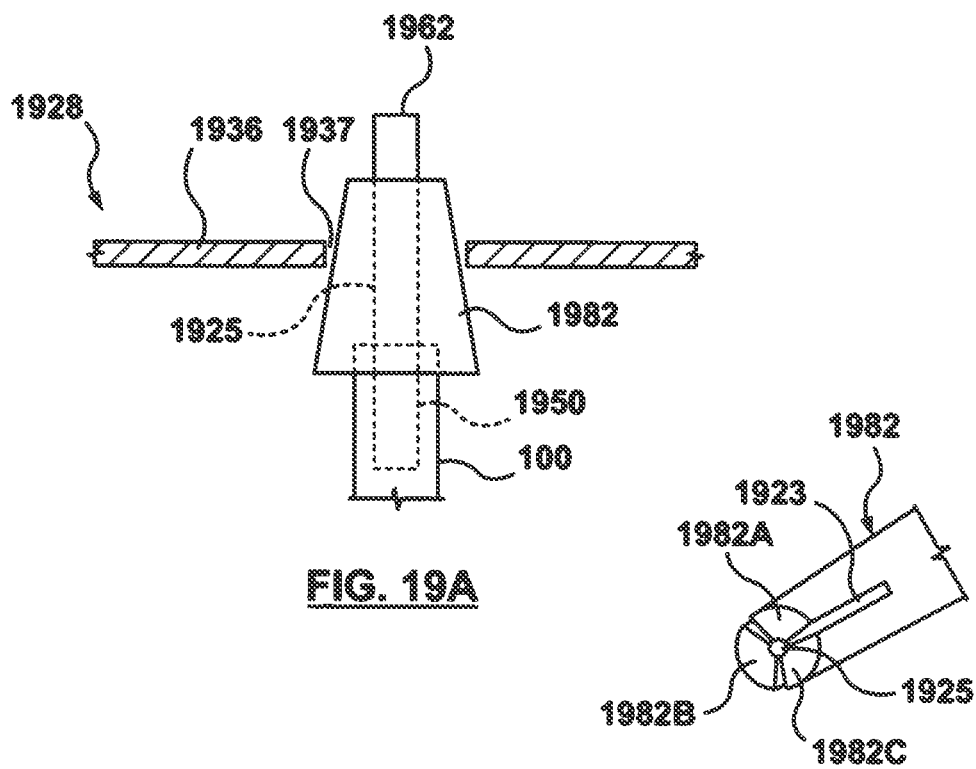
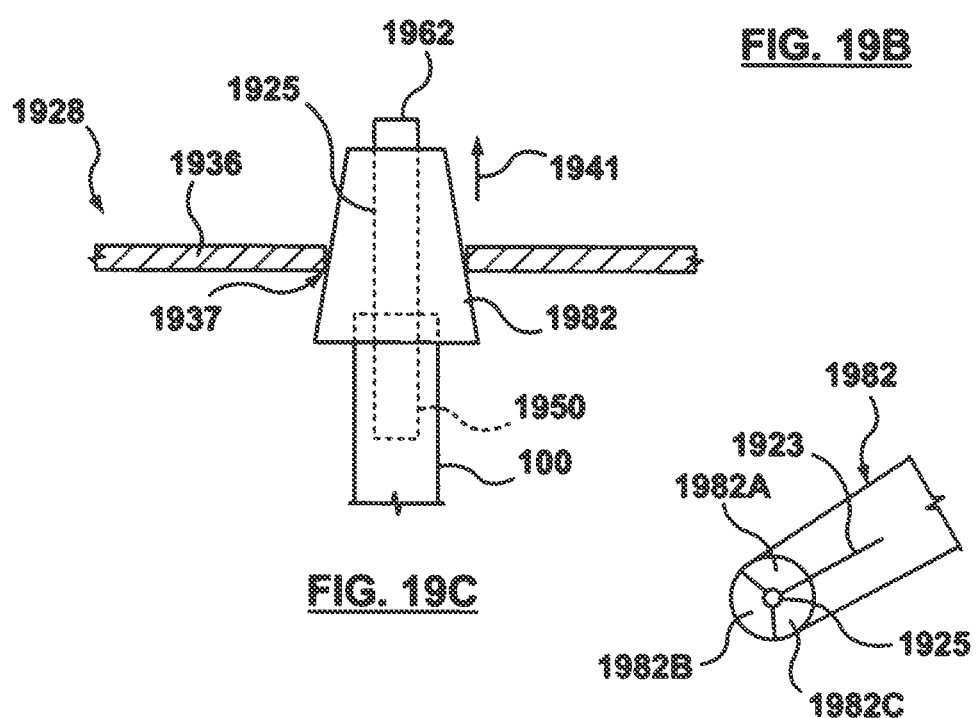

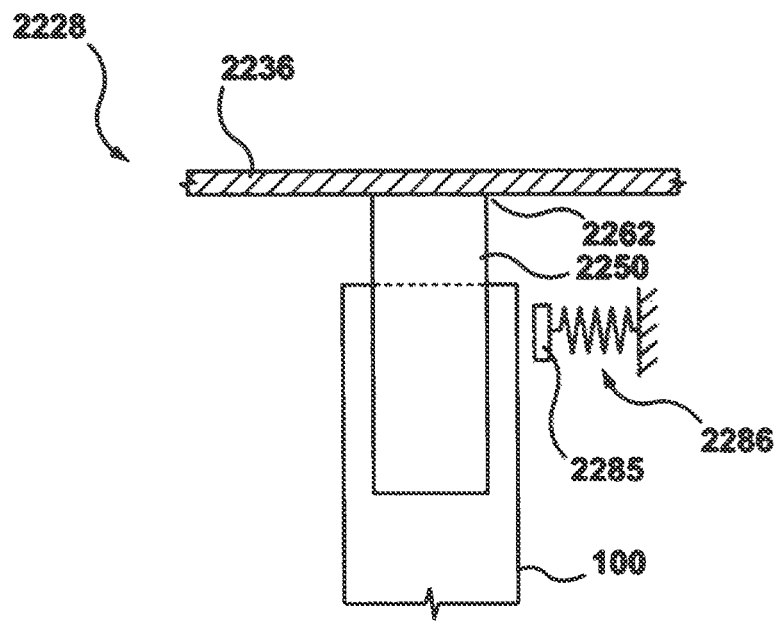
FIG. 22A
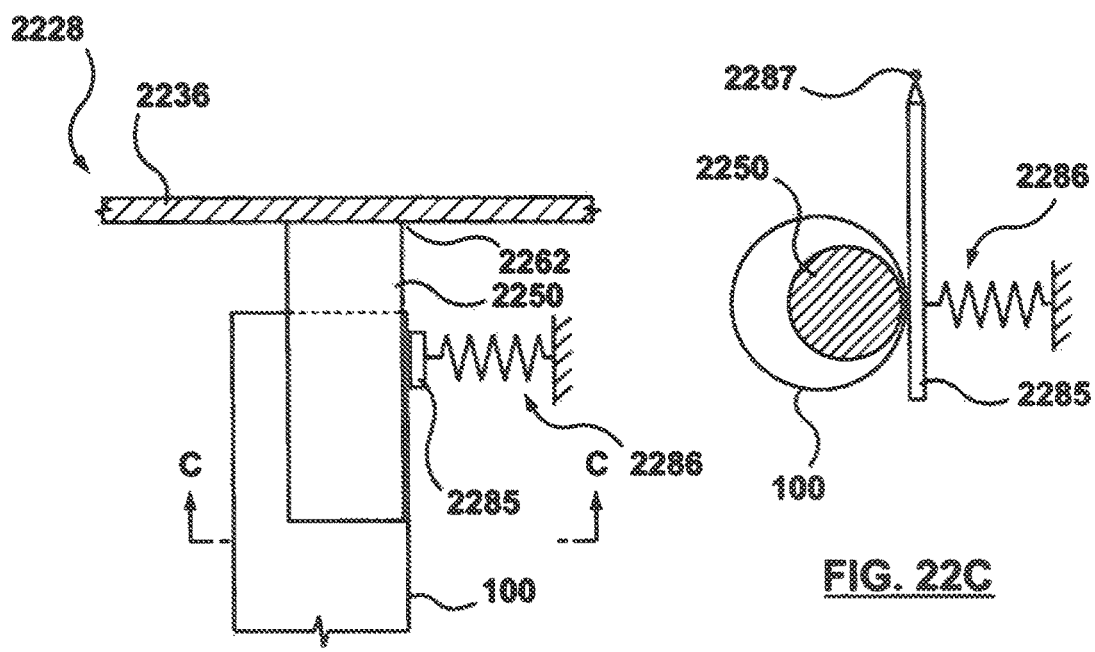
FIG. 22B
FIG. 22C

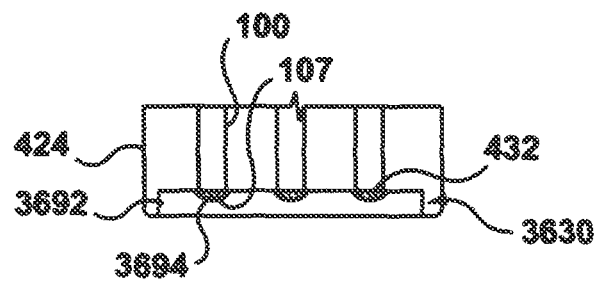
FIG. 36A
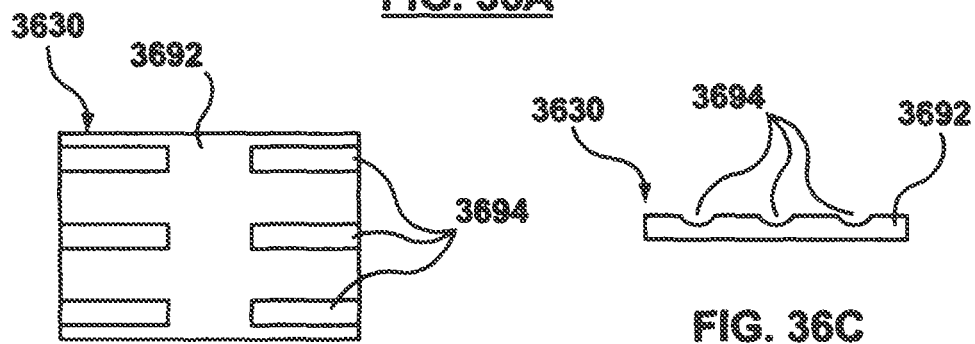
FIG. 36B
FIG. 36C
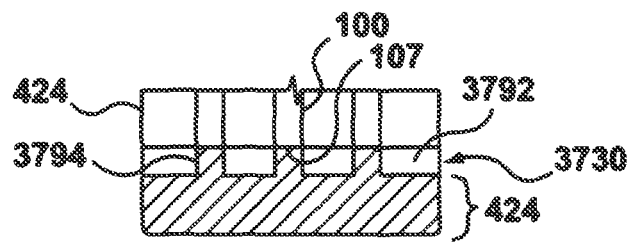
FIG. 37A
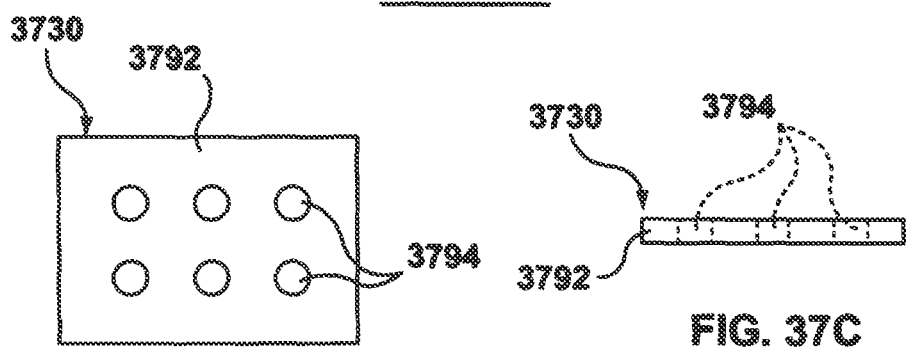
FIG. 37B
FIG. 37C

APPARATUS AND METHODS FOR FILLING A DRUG ELUTING MEDICAL DEVICE VIA CAPILLARY ACTION

RELATED APPLICATIONS

This application is a Continuation of and claims the benefit of U.S. patent application Ser. No. 13/457,398 filed Apr. 26, 2012. The disclosures of which are herein incorporated by reference in their entirety.

FIELD OF THE INVENTION

The invention relates generally to implantable medical devices that release a therapeutic substance or drug, and more particularly to apparatuses and methods of loading or filling such medical devices with the therapeutic substance or drug.

BACKGROUND OF THE INVENTION

Drug-eluting implantable medical devices are useful for their ability to provide structural support while medically treating the area in which they are implanted. For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include sirolimus and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a drug or a combination of drugs. Once the medical device is implanted at a target location, the drug is released from the polymer for treatment of the local tissues. The drug is released by a process of diffusion through a polymer layer of a biostable polymer, and/or as the polymer material degrades when the polymer layer is of a biodegradable polymer.

Drug impregnated polymer coatings are limited in the quantity of the drug to be delivered by the amount of a drug that the polymer coating can carry and the size of the medical device. As well, controlling the rate of elution using polymer coatings is difficult.

Accordingly, drug-eluting medical devices that enable increased quantities of a drug to be delivered by the medical device, and allow for improved control of the elution rate of the drug, and improved methods of forming such medical devices are needed. Co-pending U.S. Patent Application Publication No. 2011/0008405, filed Jul. 9, 2009, U.S. Provisional Application No. 61/244,049, filed Sep. 20, 2009, U.S. Provisional Application No. 61/244,050, filed Sep. 20, 2009, and co-pending U.S. Patent Application Publication No. 2012/0067008, each incorporated by reference herein in their entirety, disclose methods for forming drug-eluting stents with hollow wires. Drug-eluting stents formed with hollow wires can achieve similar elution curves as drug-eluting stents with the therapeutic substance disposed in a polymer on the surface of the stent. Drug-eluting stents formed with hollow wires achieving similar elution curves as drug-polymer coated stent are expected to have similar clinical efficacy while simultaneously being safer without the polymer coating. In addition, a variety of elution curves can be achieved from drug-eluting stents formed with hollow wires. In some applications, such as coronary stents, the diameter of the hollow wire lumen to be filled with the drug or therapeutic substance is extremely small, e.g. about 0.0015 in., which may make filling the lumen difficult. As such, improved apparatus for and methods of filling or loading a therapeutic substance or drug within a lumen of a hollow wire of a stent are needed.

BRIEF SUMMARY OF THE INVENTION

Embodiments hereof are directed to methods and apparatus for filling a fluid drug formulation within a lumenal space of a hollow wire having a plurality of side openings along a length thereof that forms a drug-eluting stent with a plurality of side drug delivery openings. In an embodiment hereof, a stent formed from a hollow wire having a plurality of side openings is placed within a first chamber of an apparatus. The apparatus includes a valve positioned between the first chamber and a second chamber that houses a wicking means that is in contact with a fluid drug formulation and the valve is closed such that the first chamber and second chamber are not in fluid communication. The valve is opened such that the first chamber and second chamber are in fluid communication. The first and second chambers reach solvent vapor saturation or near solvent vapor saturation. A portion of the stent is placed into contact with the wicking means within the second chamber such that at least one of the plurality of side openings is in contact with the wicking means. Contact between the wicking means and the selected portion of the stent is maintained until a lumenal space defined by the hollow wire is filled with the fluid drug formulation via capillary action through the at least one of the plurality of side openings in contact with the wicking means. The stent is retracted such that the portion of the stent is no longer in contact with the wicking means and is located within the first chamber. The valve is closed such that the first chamber and second chamber are not in fluid communication, and the solvent vapor pressure in the first chamber is reduced to evaporate a solvent of the fluid drug formulation.

In another embodiment hereof, a stent formed from a hollow wire having a plurality of side openings is placed within a chamber that houses a fluid drug formulation. The chamber is at or near the vapor-liquid equilibrium of a solvent of the fluid drug formulation. A portion of the stent is placed into contact with the fluid drug formulation such that at least one of the plurality of side openings is in contact with the fluid drug formulation. Contact between the fluid drug formulation and the selected portion of the stent is maintained until a lumenal space defined by the hollow wire is filled with the fluid drug formulation via capillary action through the at least one of the plurality of side openings in contact with the fluid drug formulation. A wicking means may control transfer of the fluid drug formulation into the stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 19A-19D illustrate another embodiment of a stent suspension means, which holds or secures the plurality of stents in place during the capillary filling procedure described in FIGS. 4A-7.

FIGS. 22A-22C illustrate another embodiment of a stent suspension means, which holds or secures the plurality of stents in place during the capillary filling procedure described in FIGS. 4A-7.

FIGS. 36A-36C illustrate another embodiment of a wicking means, which minimizes the contact area between each stent and the fluid drug formulation in order to control transfer of a fluid drug formulation to a stent during the capillary filling procedure described in FIGS. 4A-7.

FIGS. 37A-37C illustrate another embodiment of a wicking means, which minimizes the contact area between each stent and the fluid drug formulation in order to control transfer of a fluid drug formulation to a stent during the capillary filling procedure described in FIGS. 4A-7.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, the term "self-expanding" is used in the following description is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well, poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Drug eluting stents described herein may be utilized in the context of treatment of blood vessels such as the coronary, carotid and renal arteries, or any other body passageways where it is deemed useful. More particularly, drug eluting stents loaded with a therapeutic substance by methods described herein are adapted for deployment at various treatment sites within the patient, and include vascular stents (e.g., coronary vascular stents and peripheral vascular stents such as cerebral stents), urinary stents (e.g., urethral stents and ureteral stents), biliary stents, tracheal stents, gastrointestinal stents and esophageal stents. Furthermore, there is no intention to be bound by any expressed or implied theory presented in the preceding technical field, background, brief summary or the following detailed description.

Hollow Wire Drug-Eluting Stent

Figure 1:
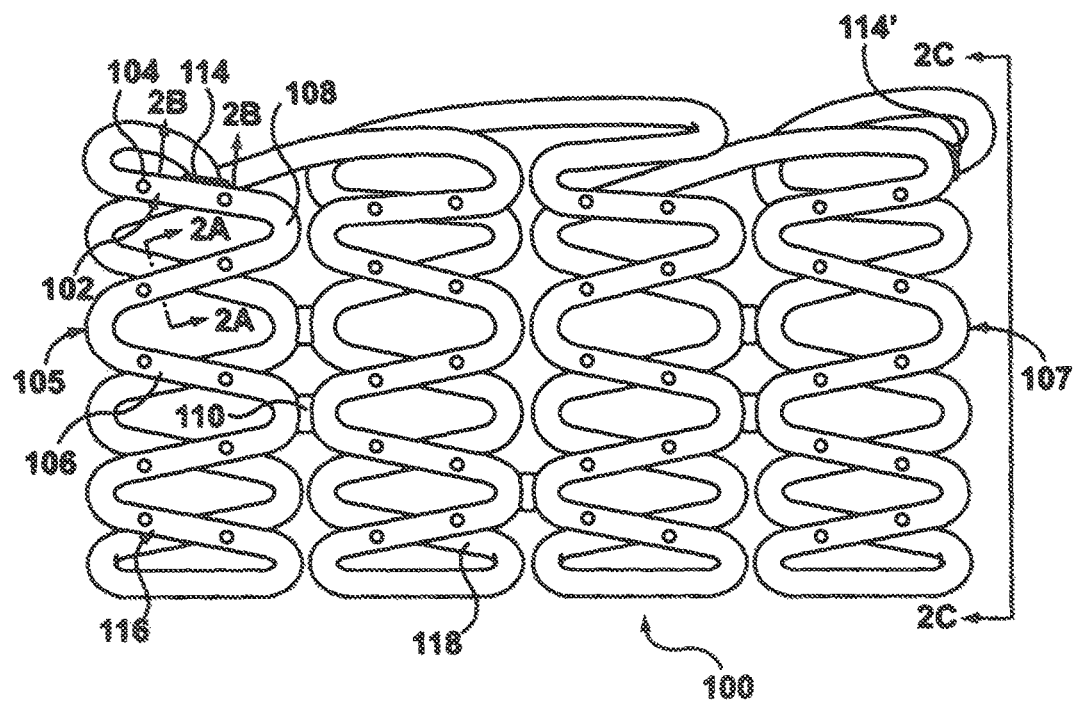
FIG. 1 is a side view of a drug eluting stent formed from a hollow wire according to one embodiment hereof.
Figures 2A, 2B, 2C:
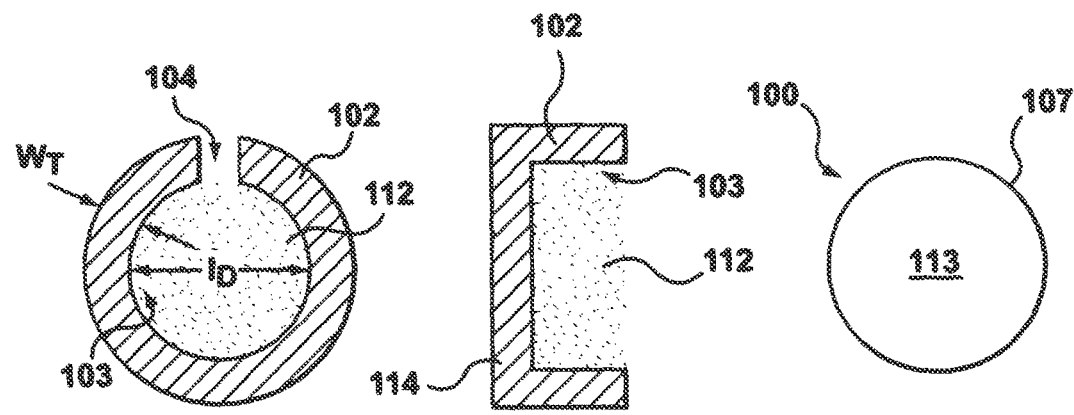
FIG. 2A is a cross-sectional view taken along line 2A-2A of FIG. 1.
FIG. 2B is a sectional view taken along line 2B-2B at an end of the hollow wire of FIG. 1.
FIG. 2C is an end view taken along line 2C-2C of FIG. 1

An embodiment of a stent 100 to be loaded with a drug in accordance with embodiments hereof is shown in FIGS. 1-2C. Stent 100 is formed from a hollow strut or wire 102 and hereinafter may be referred to as a stent or a hollow core stent. Hollow wire 102 defines a lumen or lumenal space 103, which may be formed before or after being shaped into a desired stent pattern. In other words, as used herein, "a stent formed from a hollow wire" includes a straight hollow wire shaped into a desired stent pattern or a stent constructed from any suitable manufacturing method that results in a tubular component formed into a desired stent pattern, the tubular component having a lumen or lumenal space extending continuously there through. As shown in FIG. 1, hollow wire 102 is formed into a series of generally sinusoidal waves including generally straight segments 106 joined by bent segments or crowns 108 to form a waveform that is wound around a mandrel or other forming device to form a generally cylindrical stent 100 that defines a central blood flow passageway or lumen 113 (shown in FIG. 2C) there through that extends from a first end or tip 105 to a second end or tip 107 of stent 100. Selected crowns 108 of longitudinally adjacent turns of the waveform may be joined by, for example, fusion points or welds 110 as shown in FIG. 1. Methods of filling a drug within a stent in accordance with embodiments hereof are not limited to stents having the pattern shown in FIG. 1. Stents formed into any pattern suitable for use as a stent may be loaded with a drug by the methods disclosed herein. For example, and not by way of limitation, stents formed into patterns disclosed in U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety, may be loaded with a drug by the methods disclosed herein.

As shown in FIG. 2A, hollow wire 102 of stent 100 allows for a therapeutic substance or drug 112 to be deposited within lumen or lumenal space 103 of hollow wire 102. Although lumen 103 is shown as uniformly filled with therapeutic substance or drug 112 in FIG. 2A, therapeutic substance or drug 112 is not required to fill or be uniformly dispersed within the lumenal space 103 of hollow wire 102 but is only required to occupy at least a portion of the lumenal space. Lumen 103 may continuously extend from a first end 114 to a second end 114' of hollow wire 102. Although hollow wire 102 is shown as generally having a circular cross-section, hollow wire 102 may be generally elliptical or rectangular in cross-section. Hollow wire 102 may have a wall thickness $W_T$ in the range of 0.0004 to 0.005 inch with an inner or lumen diameter $I_D$ ranging from 0.0005 to 0.02 inch. Hollow wire 102 that forms stent 100 may be made from a metallic material for providing artificial radial support to the wall tissue, including but not limited to stainless steel, nickel-titanium (nitinol), nickel-cobalt alloy such as MP35N, cobalt-chromium, tantalum, titanium, platinum, gold, silver, palladium, iridium, and the like. Alternatively, hollow wire 102 may be made from a hypotube, which is a hollow metal tube of a very small diameter of the type typically used in manufacturing hypodermic needles. Alternatively, hollow wire 102 may be formed from a non-metallic material, such as a polymeric material. The polymeric material may be biodegradable or bioresorbable such that stent 100 is absorbed in the body after being utilized to restore patency to the lumen and/or provide drug delivery.

Hollow wire 102 further includes drug-delivery side openings or ports 104 dispersed along its length to permit therapeutic substance or drug 112 to be released from lumen 103. Side openings 104 may be disposed only on generally straight segments 106 of stent 100, only on crowns 108 of stent 100, or on both generally straight segments 106 and crowns 108. Side openings 104 may be sized and shaped as desired to control the elution rate of drug 112 from stent 100. More particularly, side openings 104 may be slits or may be holes having any suitable cross-section including but not limited to circular, oval, rectangular, or any polygonal cross-section. Larger sized side openings 104 generally permit a faster elution rate and smaller sized side openings 104 generally provide a slower elution rate. Further, the size and/or quantity of side openings 104 may be varied along stent 100 in order to vary the quantity and/or rate of drug 112 being eluted from stent 100 at different portions of stent 100. Side openings 104 may be, for example and not by way of limitation, 5-30 μm in width or diameter. Side openings 104 may be provided only on an outwardly facing or abluminal surface 116 of stent 100, as shown in FIG. 2, only on the inwardly facing or lumenal surface 118 of stent 100, on both surfaces, or may be provided anywhere along the circumference of wire 102.

In various embodiments hereof, a wide range of therapeutic agents or drugs may be utilized as the elutable therapeutic substance or drug 112 contained in lumen 103 of hollow wire 102, with the pharmaceutically effective amount being readily determined by one of ordinary skill in the art and ultimately depending, for example, upon the condition to be treated, the nature of the therapeutic agent itself, the tissue into which the dosage form is introduced, and so forth. Further, it will be understood by one of ordinary skill in the art that one or more therapeutic substances or drugs may be loaded into hollow wire 102. Therapeutic substance or drug 112 delivered to the area of a stenotic lesion can be of the type that dissolves plaque material forming the stenosis or can be an anti-platelet formation drug, an anti-thrombotic drug, or an anti-proliferative drug. Such drugs can include TPA, heparin, urokinase, sirolimus or analogues of sirolimus, for example. Of course stent 100 can be used for delivering any suitable medications to the walls and interior of a body vessel including one or more of the following: anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

In accordance with embodiments hereof, stent 100 is loaded or filled with therapeutic substance or drug 112 prior to implantation into the body. Therapeutic substance or drug 112 is generally mixed with a solvent or dispersion medium/dispersant in order to be loaded into lumen 103 of hollow wire 102. In addition, the therapeutic substance or drug 112 can be mixed with an excipient to assist with elution in addition to the solvent or dispersion medium/dispersant in order to be loaded into lumen 103 of hollow wire 102. Hereinafter, the term "fluid drug formulation" may be used to refer generally to therapeutic substance or drug 112, a solvent or dispersion medium, and any excipients/additives/modifiers added thereto. In one embodiment, therapeutic substance or drug 112 is mixed with a solvent or solvent mixture as a solution before being loaded into hollow wire 102. A solution is a homogeneous mixture in which therapeutic substance or drug 112 dissolves within a solvent or a solvent mixture. In one embodiment, a solution includes a high-capacity solvent which is an organic solvent that has a high capacity to dissolve therapeutic substance or drug 112. High capacity as utilized herein is defined as an ability to dissolve therapeutic substance or drug 112 at concentrations greater than 500 mg of substance per milliliter of solvent. Examples of high capacity drug dissolving solvents for sirolimus and similar substances include but are not limited to tetrahydrofuran (THF), di-chloromethane (DCM), chloroform, and di-methyl-sulfoxide (DMSO). In addition to the high-capacity solvent, a solution may include an excipient in order to assist in drug elution. In one embodiment, an excipient may be a surfactant such as but not limited to sorbitan fatty acid esters such as sorbitan monooleate and sorbitan monolaurate, polysorbates such as polysorbate 20, polysorbate 60, and polysorbate 80, cyclodextrins such as 2-hydroxypropyl-beta-cyclodextrin and 2,6-di-O-methyl-beta-cyclodextrin, sodium dodecyl sulfate, octyl glucoside, and low molecular weight poly(ethylene glycol)s. In another embodiment, an excipient may be a hydrophilic agent such as but not limited to salts such as sodium chloride and other materials such as urea, citric acid, and ascorbic acid. In yet another embodiment, an excipient may be a stabilizer such as but not limited to butylated hydroxytoluene (BHT). Depending on the desired drug load, a low capacity solvent can also be chosen for its reduced solubility of therapeutic substance or drug 112. Low capacity is defined as an ability to dissolve therapeutic substance or drug 112 at concentrations typically below 500 mg of drug per milliliter solvent. Examples of low capacity drug dissolving solvents for sirolimus and similar substances include but are not limited to methanol, ethanol, propanol, acetonitrile, ethyl lactate, acetone, and solvent mixtures like tetrahydrofuran/water (9:1 weight ratio). After a solution is loaded into stent 100, therapeutic substance or drug 112 may be precipitated out of the solution, e.g., transformed into solid phase, and the majority of the residual solvent and any nonsolvent, if present, may be extracted from the lumenal space of hollow wire 102 such that primarily only therapeutic substance or drug 112 or therapeutic substance or drug 112 and one or more excipients remain to be eluted into the body.

In another embodiment, therapeutic substance or drug 112 is mixed with a dispersion medium as a slurry/suspension before being loaded into hollow wire 102. In a slurry/suspension form, therapeutic substance or drug 112 is not dissolved but rather dispersed as solid particulate in a dispersion medium, which refers to a continuous medium in liquid form within which the solid particles are dispersed. Examples of dispersion mediums with an inability to dissolve therapeutic substance or drug 112 depend on the properties of therapeutic substance or drug 112. For example, suitable dispersion mediums with an inability to dissolve sirolimus include but are not limited to water, hexane, and other simple alkanes, e.g., C5 thru C10. Certain excipients, suspending agents, surfactants, and/or other additives/modifiers can be added to the drug slurry/suspension to aid in suspension and stabilization, ensure an even dispersion of drug throughout the suspension and/or increase the surface lubricity of the drug particles. Surfactants thus generally prevent therapeutic substance or drug 112 from floating on the top of or sinking to the bottom of the dispersion medium. Examples of surfactants include but are not limited to sorbitan fatty acid esters such as sorbitan monooleate and sorbitan monolaurate, polysorbates such as polysorbate 20, polysorbate 60, and polysorbate 80, and cyclodextrins such as 2-hydroxypropyl-beta-cyclodextrin and 2,6-di-O-methyl-beta-cyclodextrin. In one embodiment, the targeted amount of therapeutic substance or drug 112 is suspended in the dispersion medium and the appropriate additive/modifier is added on a 0.001 to 10 wt % basis of total formulation. In addition, an excipient such as urea or 2,6-di-O-methyl-beta-cylcodextrin may be added to the slurry/suspension in order to assist in drug elution.

Open ends 114, 114' of wire 102 may be closed or sealed either before or after the drug is loaded within lumen 103 as shown in the sectional view of FIG. 2B, which is taken along line 2B-2B of FIG. 1. Once positioned inside of the body at the desired location, stent 100 is deployed for permanent or temporary implantation in the body lumen such that therapeutic substance or drug 112 may elute from lumen 103 via side openings 104.

Filling Process Via Capillary Action

Embodiments hereof relate to the use of capillary action to fill lumen 103 of hollow wire 102. Capillary action as used herein relates to the ability of a liquid to flow in narrow spaces without the assistance of, and in opposition to, external forces like gravity. As will be explained in further detail herein, only a portion of stent 100 having at least one side hole 104 is required to be submerged or exposed to a fluid drug formulation, or submerged or exposed to a wicking means in contact with a fluid drug formulation. The fluid drug formulation will then wick or travel into lumen 103 of hollow wire 102 via submerged/exposed holes 104 and fill or load the entire length of lumen 103 via capillary action. Capillary action occurs because of inter-molecular attractive forces between the fluid drug formulation and hollow wire 102. When lumen 103 of hollow wire 102 is sufficiently small, then the combination of surface tension and adhesive forces formed between the fluid drug formulation and hollow wire 102 act to lift the fluid drug formulation and fill the hollow wire. Filling stents 100 via capillary action result in a filling method that streamlines the drug filling process because such a method may be utilized to batch fill a plurality of stents in a relatively short time period. In addition, filling stents 100 via capillary action reduces drug load variability and makes the drug fill process more controllable and predictable. Capillary action results in fluid drug formulation uniformly filling or deposited within lumen 103 of hollow wire 102, and after solvent/dispersion medium extraction which is described in more detail below, lumen 103 of hollow wire 102 has a uniform drug content along its length.

Figure 3:
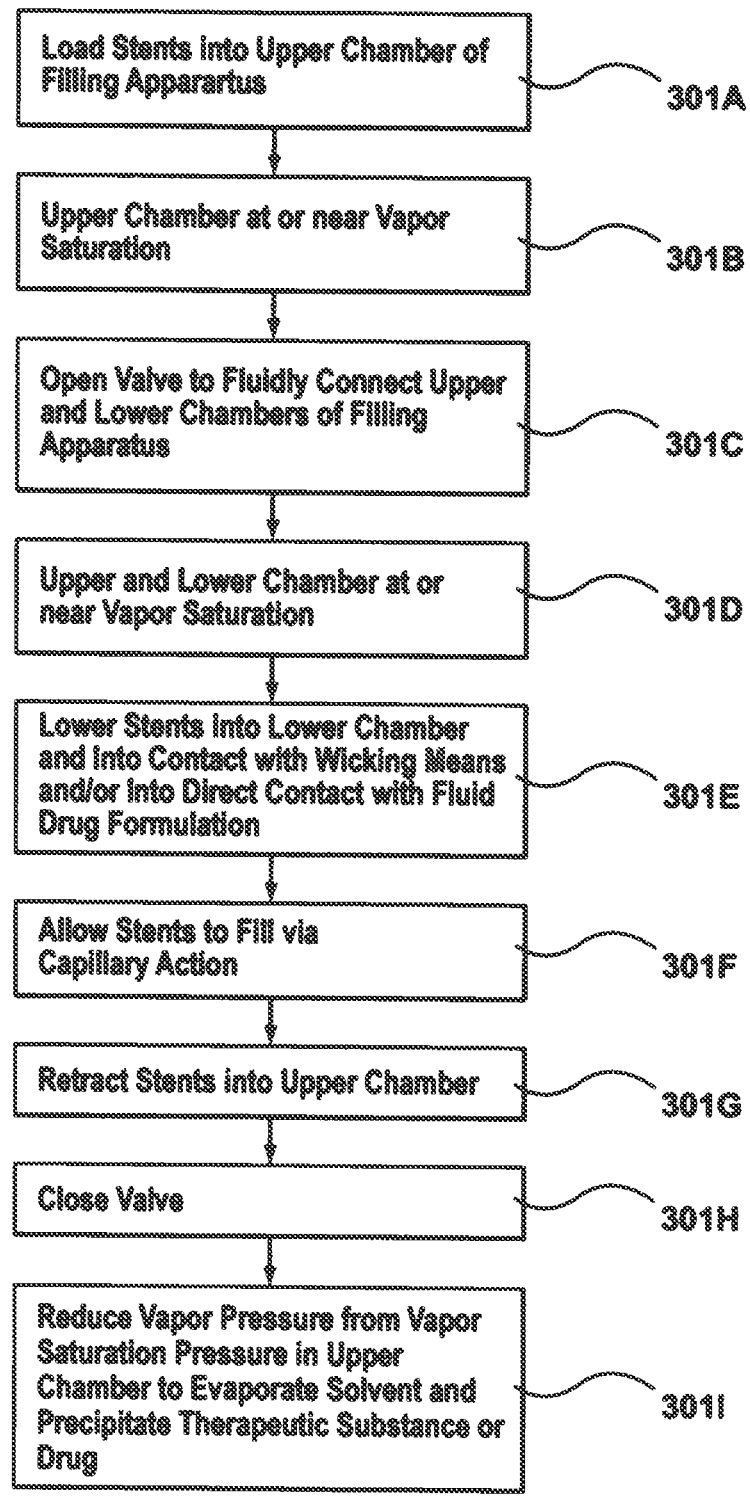
FIG. 3 is a flow chart of a method for filling a plurality of stents of FIG. 1 with a fluid drug formulation via capillary action.
Figure 4A:
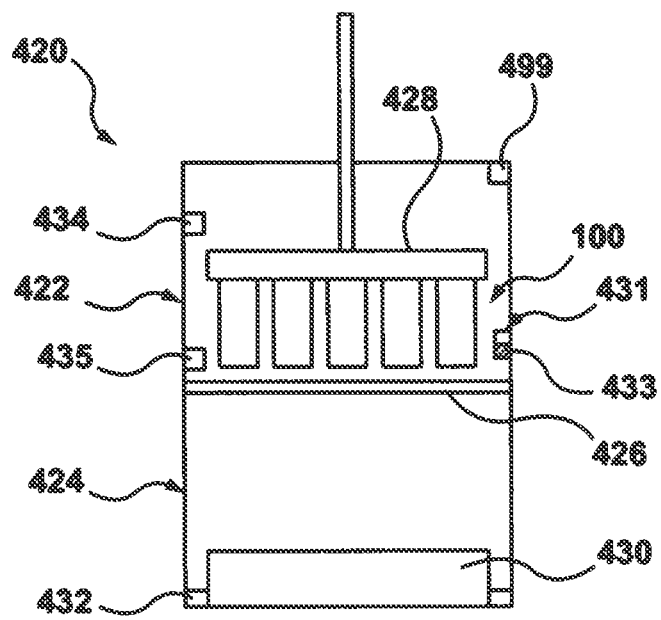
FIGS. 4A-7 are schematic illustrations of the method of the flow chart of FIG. 3 performed in an apparatus having upper and lower chambers, wherein the stents come into contact with the fluid drug formulation via a wicking means.
Figure 4B:
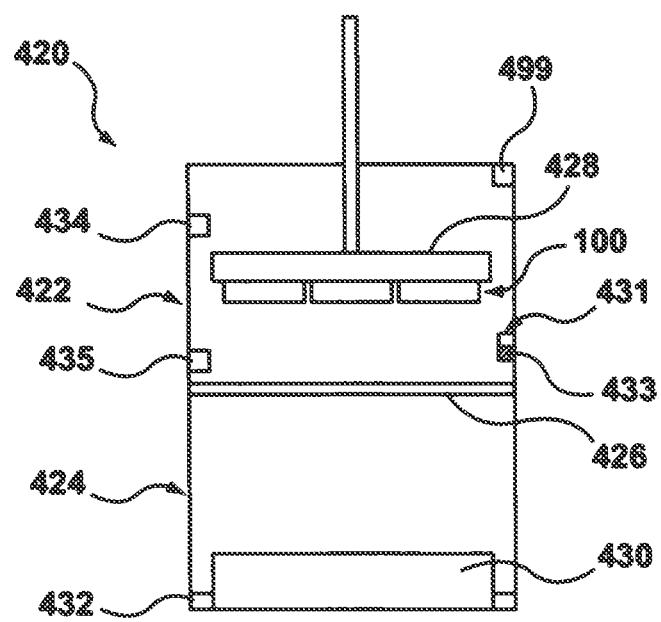
Figure 39:
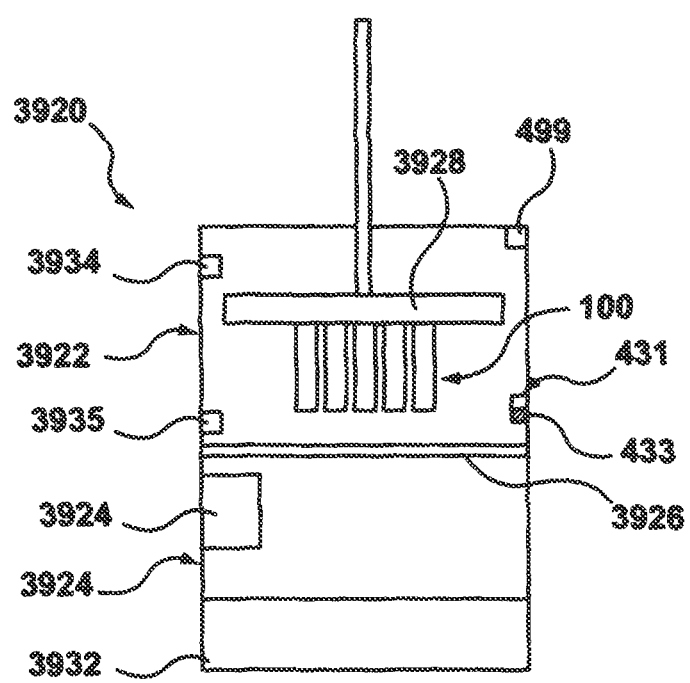
FIG. 39 is a schematic illustration of an apparatus having upper and lower chambers for performing the method of the flow chart of FIG. 3, wherein the stents come into direct contact with the fluid drug formulation without the assistance of a wicking means.

More particularly, FIG. 3 is a flow chart of a method for filling lumen 103 of a stent 100 with a fluid drug formulation 432 via capillary action. FIG. 3 will be described in conjunction with FIGS. 4A-7, which are schematic illustrations of an apparatus 420 which may be utilized to perform the method steps of FIG. 3. As will be described in more detail herein, FIGS. 4A-7 represent an embodiment hereof in which a wicking means controls the transfer of fluid drug formulation into lumen 103 while FIG. 39 represents an embodiment hereof in which the stents directly contact fluid drug formulation without a wicking means in order to fill lumen 103. For illustrative purposes only, stents 100 are represented as straight tubular structures in FIGS. 4A-7 although it will be understood by one of ordinary skill in the art that stents 100 are a hollow wire shaped into a desired stent pattern as previously described with reference to FIG. 1. Apparatus 420 includes a first or upper chamber 422 which houses a manifold or stent suspension means 428 and an open container or reservoir 431 filled with a liquid or fluid solvent 433, a second or lower chamber 424 which houses a wicking means 430 that is in contact with fluid drug formulation 432 that includes therapeutic substance or drug 112, and a valve 426 positioned between upper chamber 422 and lower chamber 424. Solvent 433 within reservoir 431 is the same solvent as used in fluid drug formulation 432. Valve 426 is operable to alternate between an open configuration in which the first chamber and second chamber are in fluid communication, and a closed configuration in which the first chamber and second chamber are not in fluid communication. A plurality of stents 100 are loaded onto stent suspension means 428, which holds or suspends them in place during the capillary filling procedure, as shown in step 301A of FIG. 3. Stent suspension means 428 may suspend stents 100 in a vertical orientation as shown in FIG. 4A, or alternatively may suspend stents 100 in a horizontal orientation as shown in FIG. 4B. Stent suspension means 428 is operable to move the plurality of stents 100 between upper and lower chambers 422, 424. The capillary filling procedures in accordance with embodiment hereof may be readily scalable as batch processes. When loaded onto stent suspension means 428, stents 100 are already formed, that is, hollow wire 102 has previously been shaped or formed into a desired waveform and formed into cylindrical stent 100 as described above with respect to FIG. 1. Alternatively, if desired, the capillary filling process may be performed on straight hollow wires prior to shaping or forming hollow wire 102 into the desired waveform and subsequent stent configuration. As will be explained in more detail herein, in an embodiment hereof, stent suspension means 428 holds stents 100 in place by slightly expanding the inner diameter of the stents, thereby increasing friction between the stents and stent suspension means 428 and minimizing undesired movement of the stents.

Figure 5:
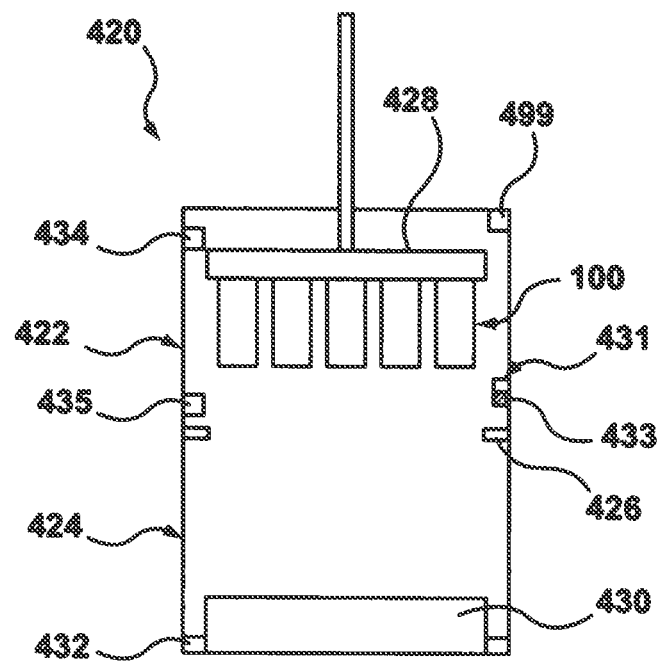

Prior to the initiation of capillary filling, with reference to FIG. 4A and/or FIG. 4B, valve 426 is closed such that first or upper chamber 422 and second or lower chamber 424 are distinct or separate closed chambers and not in fluid communication with each other. A pressure source 434 and a heat source 435 are connected to the interior of the upper chamber 422. In another embodiment (not shown), pressure source 434 and/or heat source 435 are connected to the interior of lower chamber 424, depending on the relative volume and mass differences between the chambers. Before placing stents 100 into upper chamber 422, pressure source 434 is used to purge any residual solvent vapor from the upper chamber. After the purge, stent suspension means 428 holding stents 100 are placed into upper chamber 422 and pressure source 434 is stopped to allow solvent vapor to fill upper chamber 422, as shown in step 301B of FIG. 3. When evaporation has stopped or sufficiently slowed, valve 426 is opened and so that upper and lower chambers 422, 424 are exposed to each other and in fluid communication as shown in step 301C of FIG. 3 and as shown in FIG. 5. Both upper and lower chambers 422, 424 are then required to reach solvent vapor saturation or near solvent vapor saturation, as shown in step 301D of FIG. 3. Stated another way, both upper and lower chambers 422, 424 are required to reach the vapor-liquid equilibrium of solvent 433 of fluid drug formulation 432 or near the vapor-liquid equilibrium of solvent 433. Vapor-liquid equilibrium is the condition or state where a liquid and its vapor are in equilibrium with each other, where the rate of evaporation equals the rate of condensation such that there is no net or mass transport across its respective phase. Such an equilibrium is practically reached in a relatively closed location if a liquid and its vapor are allowed to stand in contact with each other for a sufficient time period. As used herein, the term "near the vapor-liquid equilibrium" or "near solvent vapor saturation" includes pressure rates within a range of −5 torr/min to 5 torr/min. Evaporation is considered very slow and practically negligible within this range of pressure rates, and the filling process may be performed within this range of pressure rates without premature precipitation of therapeutic substance or drug 112 within lumen 103 of hollow wire 102. In a preferred embodiment hereof, the filling process is performed when the pressure rate in between −2 torr/min to 2 torr/min. Due to the step of allowing evaporation in the first or upper chamber 422 to stop or sufficiently slow prior to opening valve 426, evaporation of fluid drug formulation 432 within second or lower chamber 424 is minimized such that the formulation concentration does not change.

There are several ways to reduce the amount of time required to reach solvent vapor saturation of chambers 422, 424, thereby reducing overall processing time to increase throughput. In one embodiment, a large surface area is created to reduce the amount of time required to reach vapor saturation. In an embodiment, a large surface area may be created by atomizing droplets within upper and/or lower chamber 422, 424 with ultrasonic spray nozzles. In another embodiment, a large surface area may be created by providing wicking means 430 with a large surface area as shown in FIGS. 4A-7 in order to increase the surface area of the evaporating solvent. The amount of time required to reach vapor saturation may also be reduced by increasing the temperature of the solvent/dispersion medium. Since solvent vapor pressure is usually very dependent on temperature, heat source 435 (which may alternatively be located within second lower chamber 424) may be utilized to control the temperature of fluid drug formulation 432. The amount of time required to reach vapor saturation may also be reduced by via convection of gas across the solvent surface. For example, a fan 499 may be utilized in upper chamber 422 to create convection across reservoir 431 containing a supply of solvent 433. Reservoir 431 of solvent 433 thus supplies the vapor required to reach solvent vapor saturation. The above-described methods for reducing the amount of time required to reach solvent vapor saturation of chambers 422, 424 may be used individually or in any combination thereof.

Figure 6:
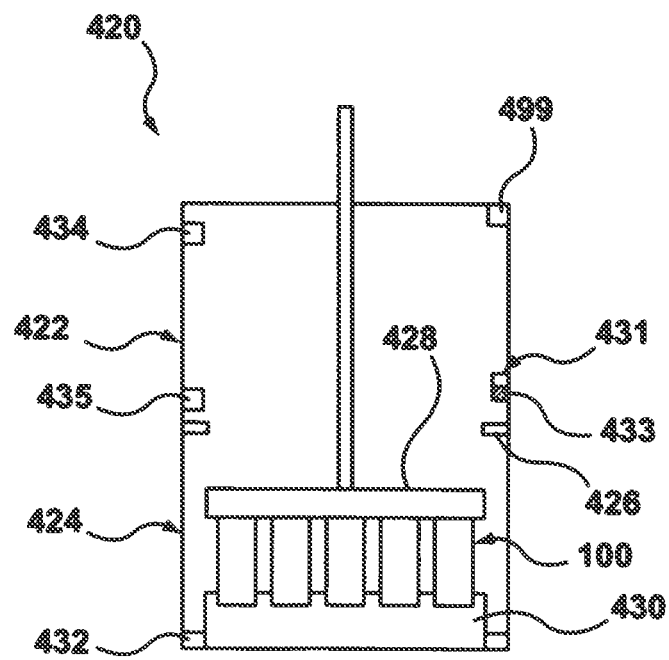

Once both chambers 422, 424 are at or near solvent vapor saturation, capillary filling may be initiated by moving stents 100 into contact with or submersed into wicking means 430 as shown in step 301E of FIG. 3 and as shown in FIG. 6. Wicking means 430 is in contact with fluid drug formulation 432, to control transfer of the fluid drug formulation into lumen 103 of hollow wire 102 of stent 100. In one embodiment, wicking means 430 is an open-celled polyurethane sponge or foam although various alternative embodiments of the wicking means are discussed herein. Stents 100 are pushed into or onto wicking means 430, thereby deforming wicking means 430. As the wicking means deforms, wicking means 430 transfers fluid drug formulation 432 from lower chamber 424 into submersed holes 104 of stent 100. Lumen 103 of hollow wire 102 of stent 100 is filled by surface tension driving fluid drug formulation 432 through the stent lumen, until the entire length of lumen 103 is filled via capillary action forces, as shown in step 301F of FIG. 3. During the filling step, chambers 422, 424 are maintained at or near the vapor-liquid equilibrium of solvent 433 such that evaporation does not precipitate therapeutic substance or drug 112 as fluid drug formulation 432 fills lumen 103 of hollow wire 102 of stents 100.

Figure 6A:
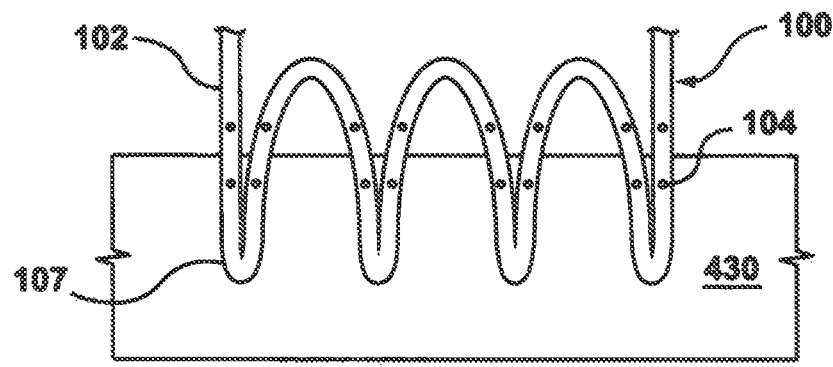
Figure 6B:
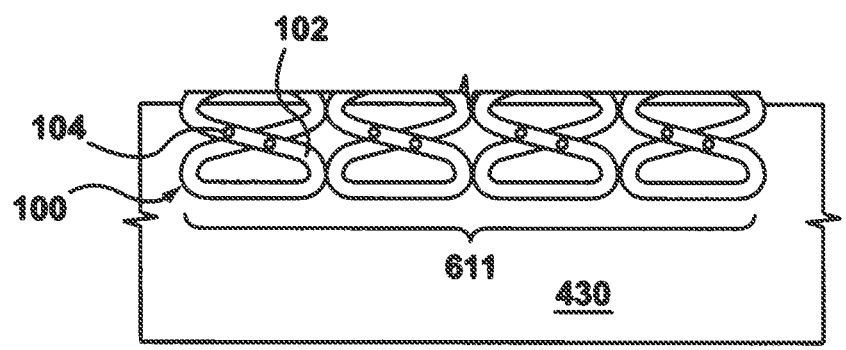
Figure 6C:
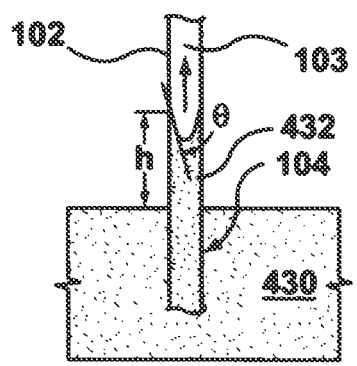

FIGS. 6A-6C are schematic illustrations of a portion of a stent 100 submersed or in contact with wicking means 430 to demonstrate the capillary filling process. Notably, only a portion of each stent having at least one side hole or port 104 is required to be submersed into wicking means 430. As such, a minimal amount of the exterior surfaces of wires 102 of stents 100 are exposed to the fluid drug formulation and most of the exterior surface of the hollow wire of the stent is never exposed to the fluid drug formulation, therefore not requiring additional cleaning or removal of drug residue. FIG. 6A corresponds to FIG. 4A, in which stent suspension means 428 hold stents 100 in a vertical orientation. When held vertically, only a tip 107 of each stent 100 is submersed into wicking means 430 such that at least one side hole 104 is in contact with wicking means 430 and exposed to fluid drug formulation 432. For example, in an embodiment, approximately 0.3 mm of the length of each stent is exposed or driven into to the wicking means. FIG. 6B corresponds to FIG. 4B, in which stent suspension means 428 hold stents 100 in a horizontal orientation. When held horizontally, a longitudinal strip or segment 611 along an outer surface of each stent 100 is submersed into wicking means 430 such that at least one side hole 104 is in contact with wicking means 430 and exposed to fluid drug formulation 432. Regardless of how stents 100 are oriented, fluid drug formulation 432 passes through hole(s) 104 on hollow wire 102 that are in contact with wicking means 430 as shown in FIG. 6C, which illustrates only a portion of hollow wire 102 having a side hole 104 submersed into wicking means 430. Fluid drug formulation 432 forms a concave meniscus within lumen 103 of hollow wire 102. Adhesion forces pull fluid drug formulation 432 up until there is a sufficient mass of fluid drug formulation 432 present for gravitational forces to overcome the intermolecular forces between fluid drug formulation 432 and hollow wire 102, or the advancing fluid column completely fills the lumen. The height h of a column of fluid drug formulation 432 is determined by $$h = \frac{2\gamma \cos\theta}{\rho g r},$$

where γ is the liquid-air surface tension (force/unit length), θ is the contact angle, ρ is the density of fluid drug formulation 432 (mass/volume), g is local gravitational field strength (force/unit mass), and r is the radius of hollow wire 102 (length). Due to the nature of capillary filling and the intermolecular forces between fluid drug formulation 432 and hollow wire 102, fluid drug formulation 432 does not exit or leak out of non-submersed holes or ports 104 that occur along the length of the stent as fluid drug formulation 432 fills lumen 103 of hollow wire 102.

The time required to fill the entire length of lumen 103 of hollow wire 102 of stent 100 depends upon the stent configuration and length. Fill time depends upon various factors, including but not limited to the length of hollow wire 102, the size of holes 104, the number of submersed holes 104, the size of lumen 103, and the properties of fluid drug formulation 432. For example, in an embodiment in which 0.3 mm length of a vertically-oriented 3 mm×18 mm stent is placed into contact with an open-celled polyurethane sponge wicking means, which is in contact with a fluid drug formulation including rapamycin dissolved in methanol, filling time is approximately 22 minutes. If it is desired to reduce the overall fill time, the number of submersed holes 104 may be increased. Often, horizontal orientation of stents may be utilized if it is desired to place a greater number of side holes into contact with the wicking means and thereby reduce the overall fill time. However, horizontal orientation of stents may expose a greater amount of the exterior surfaces of wires 102 of stents 100 to the fluid drug formulation.

Figure 7:
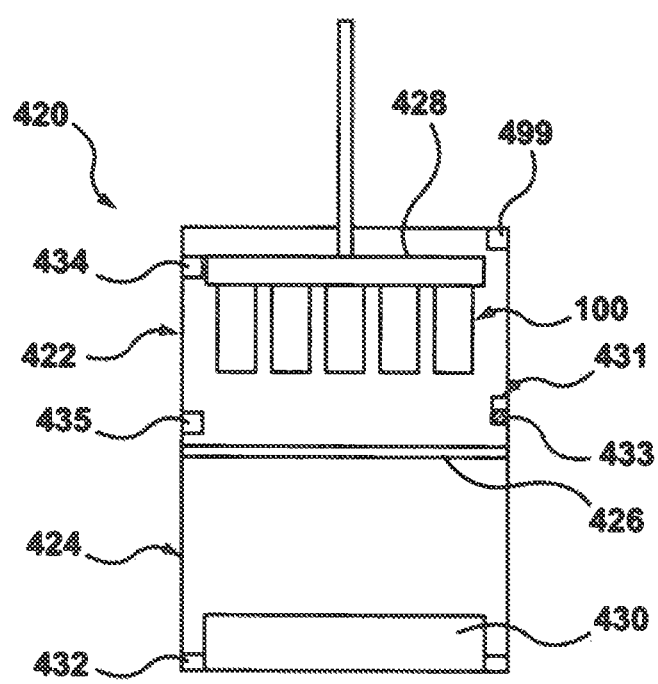

After lumen 103 is completely filled, with reference to FIG. 7, stents 100 are retracted or pulled up such that stents 100 are no longer in contact with wicking means 430. As stents 100 are retracted out of wicking means 430, wicking means 430 removes excess fluid drug formulation 432 from the exterior surfaces of wires 102 of stents 100 such that stents 100 are free or substantially free of drug residue on their exterior surfaces, leaving fluid drug formulation 432 only within lumen 103 of hollow wire 102 of stent 100. The final step of the capillary action filling process includes extracting the solvent or dispersion medium of fluid drug formulation 432 from within the lumenal space, thereby precipitating the solute, i.e., therapeutic substance or drug 112, within lumen 103 and creating a drug-filled stent 100 with primarily only therapeutic substance or drug 112 and one or more excipients within stent 100 to be eluted into the body. More particularly, stents 100 are retracted into upper chamber 422, which is still at or near vapor-liquid equilibrium of solvent 433, as shown in step 301G of FIG. 3. Valve 426 is then closed such that the chambers 422, 424 are no longer in fluid communication as shown in step 301H of FIG. 3 and as shown in FIG. 7. Valve 426 is closed to isolate fluid drug formulation 432 from the upper chamber 422 so that evaporation does not occur from the fluid drug formulation and additional batches of stents may be filled with the same fluid drug formulation without concentration changes. Upper chamber 422 is then vented to reduce its solvent vapor pressure back to ambient pressure, as shown in step 301I of FIG. 3. As the solvent vapor pressure is reduced in the upper chamber, evaporation within lumen 103 of hollow wire 102 is initiated and the solvent of drug fluid formulation 432 is removed, thereby precipitating its constituents. After the solvent or dispersion medium is removed from lumen 103, therapeutic substance or drug 112 fills at least a portion of lumen 103. Stents 100 may then be removed from apparatus 420.

Means for Holding Stents

FIGS. 8A-22B illustrate several embodiments of stent suspension means 428, which holds or secures the plurality of stents in place during the capillary filling procedure as described with reference to FIGS. 4A-7. Stent suspension means 428 serves several functions, including holding one or more stents in such a manner that only a portion of stents 100 are exposed to fluid drug formulation 432. In addition, stent suspension means 428 is preferably configured to simultaneously hold a plurality of stents 100 such that the batch size of a capillary filling procedure is readily scalable. In embodiments described below, the stent suspension means firmly and securely holds stents 100 in place by slightly expanding the inner diameter of the stents and deforming elastically, thereby increasing friction between the stents and the stent suspension means and minimizing undesired movement of the stents. When stents 100 are being positioned on stent suspension means 428, stents 100 may be secured in an array (not shown) having a plurality of wells each sized to accommodate. The array may be positioned in first or upper chamber 422 of apparatus 420, and is configured to hold stents 100 stationary while stent suspension means 428 are operated as described herein to hold stents 100 in place during the filling process. For illustrative purposes only, stents 100 are represented as straight tubular structures in FIGS. 8A-22B although it will be understood by one of ordinary skill in the art that stents 100 are a hollow wire shaped into a desired stent pattern as previously described with reference to FIG. 1. In addition, for illustrative purposes, the stent suspension means described in FIGS. 8A-22B are shown as holding stent 100 in a vertical orientation but may be modified to hold stent 100 in a horizontal orientation as described herein with reference to FIG. 4B.

Figure 8A:
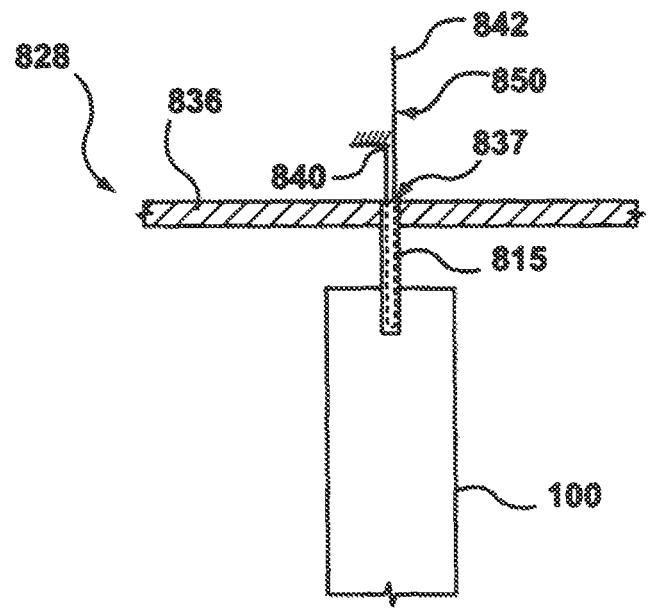
FIGS. 8A-8B illustrate an embodiment of a stent suspension means, which holds or secures the plurality of stents in place during the capillary filling procedure described in FIGS. 4A-7.
Figure 8B:
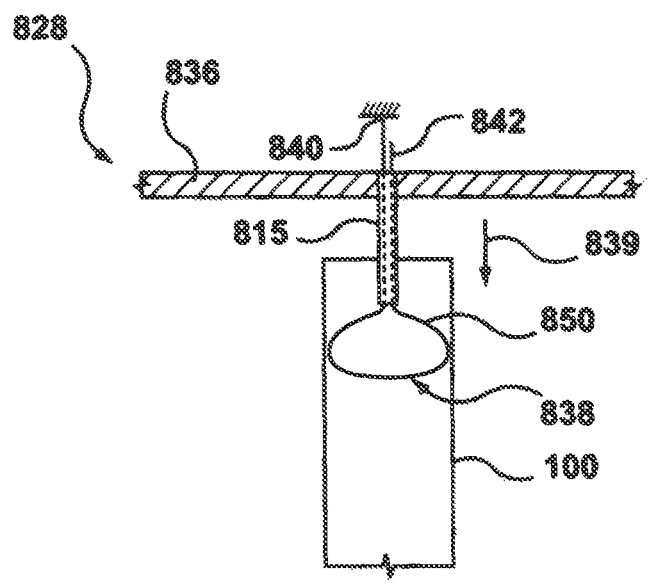

FIGS. 8A and 8B depict a stent suspension means 828 that includes a header or carousel 836, a portion of which is shown in the figure, and a mandrel wire 850 for holding a stent 100 in place during the capillary filling procedure described with reference to FIGS. 4A-7. Although only one mandrel wire 850 is shown, it will be understood by one of ordinary skill in the art that a plurality of mandrel wires may be coupled or attached to header or carousel 836 for accommodating a plurality of stents 100. Header or carousel 836 is a generally flat sheet-like component having at least one hole or passageway 837 formed there through to allow for passage of mandrel 850. Mandrel wire 850 is an elongated component having a first end 840 fixed above header or carousel 836 and a second end 842 movable relative to header or carousel 836. Mandrel wire 850 extends through a tubular component or shaft 815, which is coupled or attached to header 836 such that a lumen thereof is aligned with a passageway 837. Mandrel wire 850 extends through the lumen of shaft 815, with both first and second ends 840, 842 extending out of a top or first end thereof. Second end 842 of mandrel wire 850 may be advanced to cause a loop 838 thereof to extend out of a second or bottom end of shaft 815. Loop 838 becomes larger or smaller based on a position of second end 842 relative to shaft 815. In operation, stent 100 is positioned over shaft 815, with mandrel wire 850 being contained within the shaft as shown in FIG. 8A. Once stent 100 is in position, second end 842 is moved toward header or carousel 836 in a "downward" direction, as indicated by directional arrow 839, towards stent 100, to expose loop 828 out of shaft 815 and to increase or expand the diameter of loop 838 until the loop 838 abuts against or is in opposition with the inner diameter of stent 100 as shown in FIG. 8B. The expanded loop 838 thus grabs onto the inner diameter of stent 100, and in one embodiment, may slightly expand the inner diameter of stent 100 to increase friction between stent 100 and stent suspension means 828 to minimize undesired movement of stent 100. Loop 838 is formed from an elastic material, including but not limited to Nitinol or spring steel.

Figure 9A:
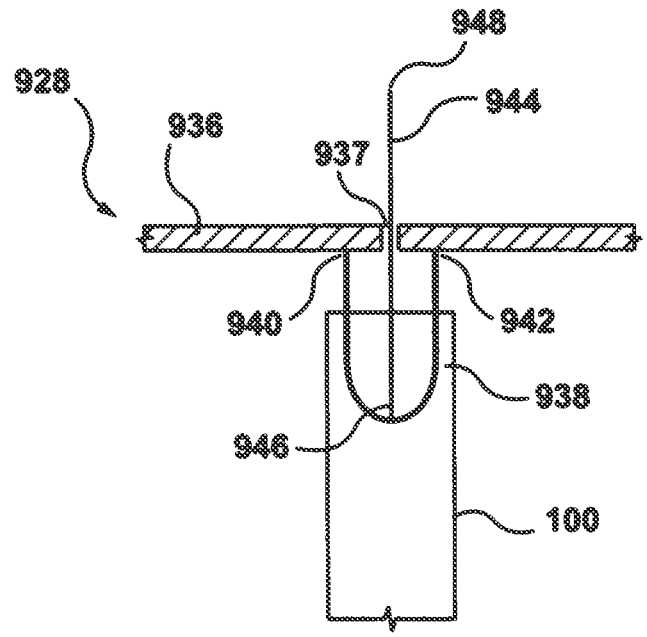
FIGS. 9A-9B illustrate another embodiment of a stent suspension means, which holds or secures the plurality of stents in place during the capillary filling procedure described in FIGS. 4A-7.
Figure 9B:
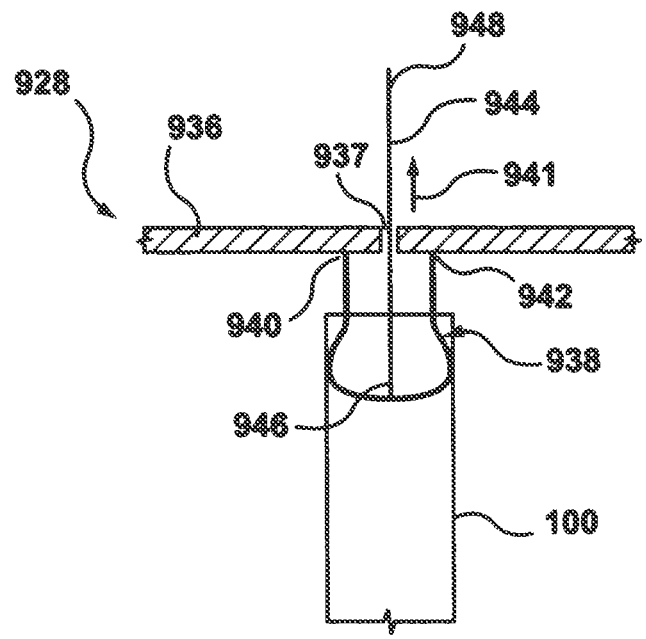

FIGS. 9A-9B illustrate another embodiment of a stent suspension means 928 that includes a header or carousel 936, a portion of which is shown in the figure, and a loop 938 for holding a stent 100 in place during the capillary filling procedure described with reference to FIGS. 4A-7. Although only one wire loop 938 is shown, it will be understood by one of ordinary skill in the art that a plurality of wire loops may be coupled to header or carousel 936 for accommodating a plurality of stents 100. Header or carousel 936 is a generally flat sheet-like component having a loop or u-shaped component 938 coupled thereto, with a first end 940 and a second end 942 of loop 938 both coupled or attached or bonded to header or carousel 936. A push-pull rod or wire 944 has a first end coupled to loop 938, at approximately the midpoint thereof, and a second end 948 which extends through a hole or passageway 937 formed through header or carousel 936. Second end 948 of push-pull wire 944 may be pushed or pulled relative to header or carousel 936 to adjust the size or diameter of loop 938. In operation, second end 948 of push-pull wire 944 is positioned to form a relatively small diameter loop 938 that fits within the inner diameter of stent 100 as shown in FIG. 9A. Once in position, second end 948 of push-pull wire 944 is moved in an "upward" direction relative to header or carousel 936, as indicated by directional arrow 941, away from stent 100, causing loop 938 to bow outwards. Movement of push-pull wire 944 causes the diameter of loop 938 to increase or expand until loop 938 abuts against or is in opposition with the inner diameter of stent 100 as shown in FIG. 9B. The larger, expanded loop 938 shown in FIG. 9B thus grabs onto the inner diameter of stent 100, and in one embodiment, may slightly expand the inner diameter of stent 100 to increase friction between stent 100 and stent suspension means 928 to minimize undesired movement of stent 100. Loop 938 is formed from an elastic material, including but not limited to Nitinol or spring steel. Although FIGS. 9A-9B are shown with only one loop attached thereto for grabbing onto the inner diameter of stent 100, one or more additional loops may be provided and equally spaced around the inner diameter of stent 100 to grab stent 100 in a more circumferential manner.

Figure 10:
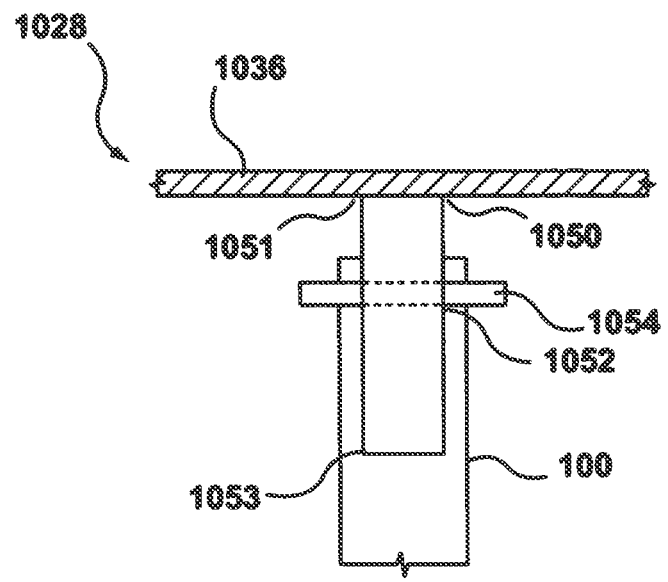
FIG. 10 illustrates another embodiment of a stent suspension means, which holds or secures the plurality of stents in place during the capillary filling procedure described in FIGS. 4A-7.

FIG. 10 illustrates another embodiment of a stent suspension means 1028 that includes a header or carousel 1036, a portion of which is shown in the figure, and a mandrel 1050 for holding a stent 100 in place during the capillary filling procedure described with reference to FIGS. 4A-7. Although only one mandrel 1050 is shown, it will be understood by one of ordinary skill in the art that a plurality of mandrels may be coupled to header or carousel 1036 for accommodating a plurality of stents 100. Header or carousel 1036 is a generally flat sheet-like component, and a first end 1051 of mandrel 1050 is coupled or attached to header or carousel 1036. Mandrel 1050 is a solid tubular component having an outer diameter which is less than the inner diameter of stent 100, so that mandrel 1050 fits inside stent 100 such that a second end 1053 of mandrel 1050 extends within stent 100. Mandrel 1050 also includes a slot or passageway 1052 formed there through, and a removable dowel rod 1054 extends through passageway 1052. Dowel rod 1054 has a length greater than the outer diameter of mandrel 1050, such that the ends of dowel rod 1054 extend beyond or past the outer diameter of mandrel 1050. The diameter of dowel rod 1054 is sufficiently small to pass through openings of stent 100 that are formed between the series of generally sinusoidal waves of stent 100. Stent 100 thus hangs on dowel rod 1054, being held in place by the interference between hollow wire 102 of stent 100 and dowel rod 1054. Dowel rod 1054 and mandrel 1050 may be connected by a slip fit or spring-release mechanism (not shown) that allows dowel rod 1054 to extrude out of the mandrel and through openings of the stent. Dowel rod 1054 and mandrel 1050 may be formed of any suitable material that is chemically compatible with organic solvents such as but not limited to stainless steel, aluminum, or select polymers including delrin and polystyrene. In another embodiment (not shown), rather than removable dowel rod 1054, tabs or similar structures may be coupled to mandrel 1050 and extend perpendicular to the longitudinal axis of stent 100 to pass through the openings of the stent.

Figure 11:
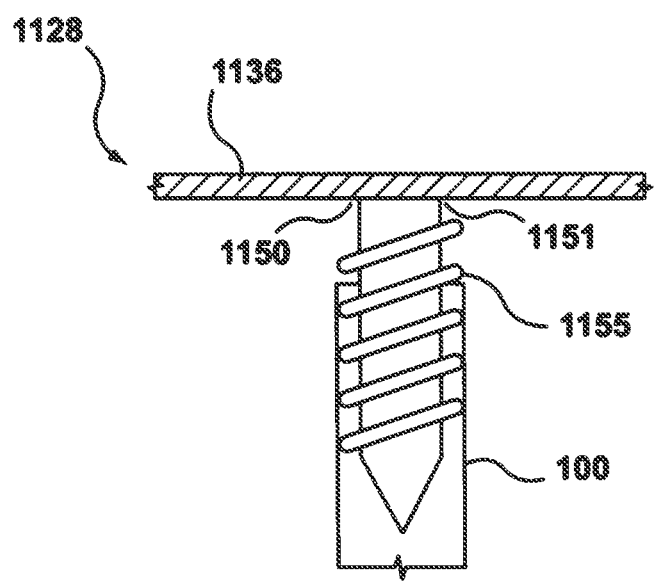
FIG. 11 illustrates another embodiment of a stent suspension means, which holds or secures the plurality of stents in place during the capillary filling procedure described in FIGS. 4A-7.

FIG. 11 illustrates another embodiment of a stent suspension means 1128 that includes a header or carousel 1136, a portion of which is shown in the figure, and a mandrel 1150 for holding a stent 100 in place during the capillary filling procedure described with reference to FIGS. 4A-7. Although only one mandrel 1150 is shown, it will be understood by one of ordinary skill in the art that a plurality of mandrels may be coupled to header or carousel 1136 for accommodating a plurality of stents 100. Header or carousel 1136 is a generally flat sheet-like component, and a first end 1151 of mandrel 1150 is coupled or attached to header or carousel 1136. Mandrel 1150 is a solid tubular component having male threads 1155 formed on an exterior surface thereof, the male threads having an outer diameter which is approximately equal to or slightly greater than the inner diameter of stent 100. Male threads 1155 engage or grip onto the inner diameter of stent 100, similar to a wood or drywall screw. Male threads 1155 may be formed from steel, and may be integrally formed on mandrel 1150 or may be a separate component coupled thereto.

Figure 12A:
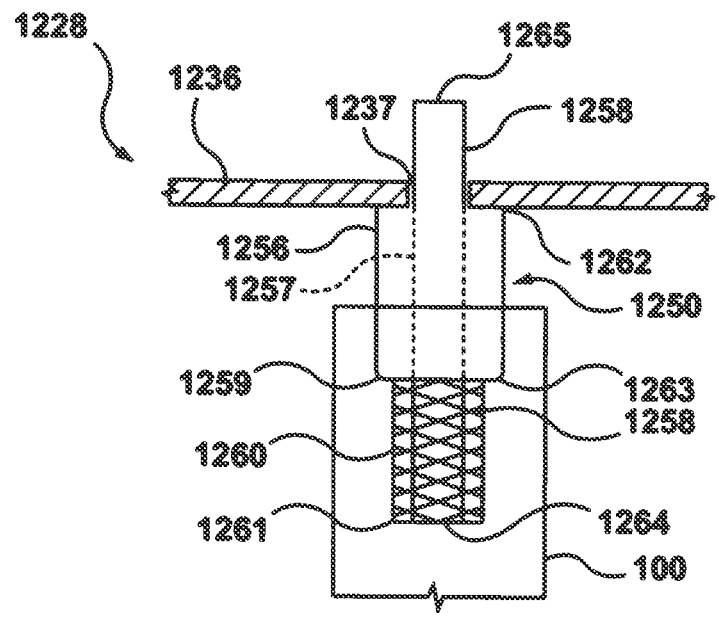
FIGS. 12A-12B illustrate another embodiment of a stent suspension means, which holds or secures the plurality of stents in place during the capillary filling procedure described in FIGS. 4A-7.
Figure 12B:
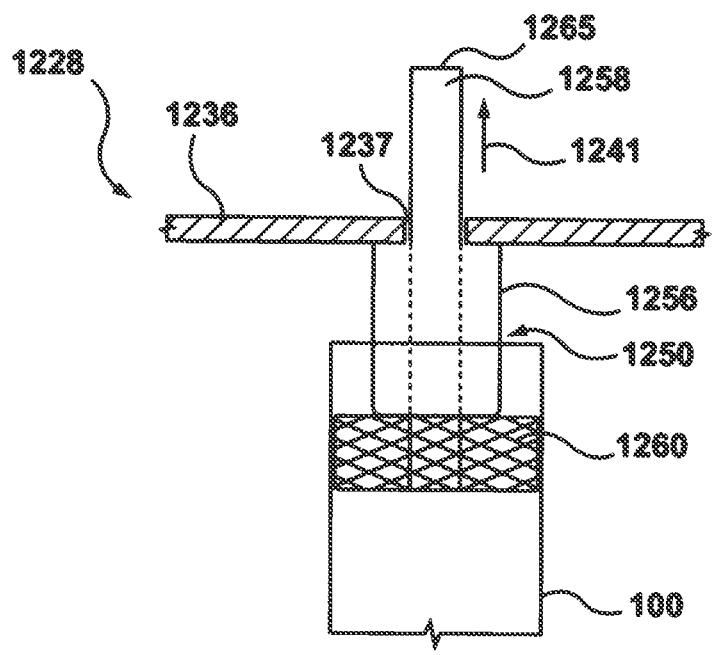

FIGS. 12A-12B illustrate another embodiment of a stent suspension means 1228 that includes a header or carousel 1236, a portion of which is shown in the figure, and a mandrel 1250 for holding a stent 100 in place during the capillary filling procedure described with reference to FIGS. 4A-7. Although only one mandrel 1250 is shown, it will be understood by one of ordinary skill in the art that a plurality of mandrels may be coupled to header or carousel 1236 for accommodating a plurality of stents 100. Header or carousel 1236 is a generally flat sheet-like component having at least one hole or passageway 1237 formed there through to allow for passage of a portion of mandrel 1250. Mandrel 1250 includes two concentric tubes or shafts, an outer tube 1256 and an inner tube 1258 slidably mounted within a lumen 1257 defined by outer tube 1256. A first end 1262 of outer tube 1256 is coupled to header or carousel 1236, and inner tube 1258 is longer than outer tube 1256 such that a first end 1265 of inner tube 1258 extends beyond first end 1262 of outer tube 1256 and through passageway 1237 of header or carousel 1236 and a second end 1264 of inner tube 1258 extends beyond a second end 1263 of outer tube 1256. A braided wire tubular or cylindrical component 1260 has a first end 1259 coupled to second end 1263 of outer tube 1256 and a second end 1261 coupled to second end 1264 of inner tube 1258. Inner tube 1258 may be pushed or pulled relative to outer tube 1256 to adjust the size or outer diameter of braided component 1260. In operation, second end 1265 of inner tube 1258 is positioned to fully extend or lengthen braided component 1260 such that the diameter of braided component 1260 fits within the inner diameter of stent 100 as shown in FIG. 12A. Once stent 100 is in position as desired, second end 1265 of inner tube 1258 is moved in an "upward" direction toward header or carousel 1236, as indicated by directional arrow 1241, away from stent 100, causing braided component 1260 to radially expand. Movement of inner tube 1258 relative to outer tube 1256 causes the diameter of braided component 1260 to increase or expand until braided component 1260 abuts against or is in opposition with the inner diameter of stent 100 as shown in FIG. 12B. The larger, braided component 1260 thus grabs onto the inner diameter of stent 100, and in one embodiment, may slightly expand the inner diameter of stent 100 to increase friction between stent 100 and stent suspension means 1228 to minimize undesired movement of stent 100. To release stent 100, inner tube 1258 is moved relative to outer tube 1256 in an "downward" direction, toward stent 100, to longitudinally extend braided component 1260 back to the position shown in FIG. 12A. Braided component 1260 is formed from a superelastic material, including but not limited to Nitinol or stainless steel, and tubes 1256, 1258 may be formed from stainless steel or a polymeric material such as but not limited to PEEK, polyimide, or PTFE.

Figure 13A:
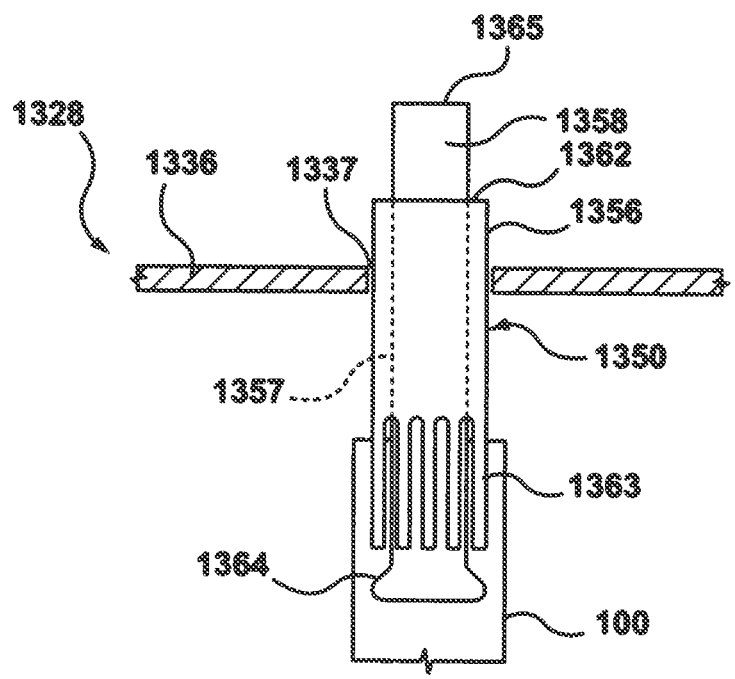
FIGS. 13A-13B illustrate another embodiment of a stent suspension means, which holds or secures the plurality of stents in place during the capillary filling procedure described in FIGS. 4A-7.
Figure 13B:
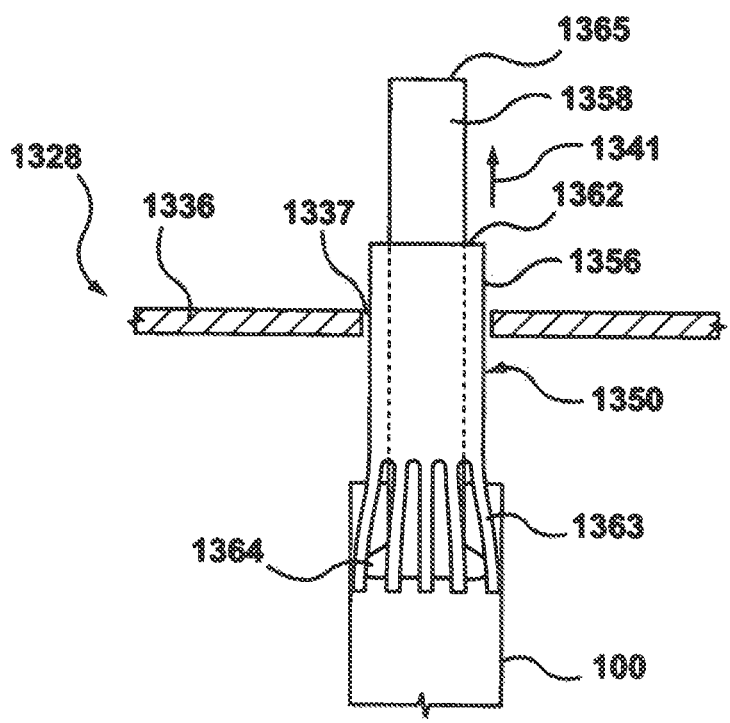

FIGS. 13A-13B illustrate another embodiment of a stent suspension means 1328 that includes a header or carousel 1336, a portion of which is shown in the figure, and a mandrel 1350 for holding a stent 100 in place during the capillary filling procedure described with reference to FIGS. 4A-7. Although only one mandrel 1350 is shown, it will be understood by one of ordinary skill in the art that a plurality of mandrels may be coupled to header or carousel 1336 for accommodating a plurality of stents 100. Header or carousel 1336 is a generally flat sheet-like component having at least one hole or passageway 1337 formed there through to allow for passage of a portion of mandrel 1350. Mandrel 1350 includes two concentric tubes or shafts that extend through passageway 1337 of header or carousel 1336, an outer tube 1356 and an inner tube 1358 slidably mounted to extend through a lumen 1357 defined by outer tube 1356. Inner tube 1358 is longer than outer tube 1356 such that a first end 1365 of inner tube 1358 extends beyond first end 1362 of outer tube 1356 and a second end 1364 of inner tube 1358 extends beyond a second end 1363 of outer tube 1356. Outer tube 1356 may be a Nitinol tube, and second end 1363 of outer tube 1356 includes a plurality of fingers, similar to a collet. Second end 1364 of inner tube 1358 is bulbous or flared, meaning that it has an outer diameter which is greater than the rest of inner tube 1358. The outer diameter of second end 1364 of inner tube 1358 is greater than the inner diameter of outer tube 1356. Inner tube 1358 may be pushed or pulled relative to outer tube 1356 to radially deploy the fingers formed on second end 1363 of outer tube 1356. In operation, second end 1365 of inner tube 1358 is positioned such that the bulbous second end 1364 of inner tube 1358 is not in contact with the fingers formed on second end 1363 of outer tube 1356 as shown in FIG. 13A. Once stent 100 is in position as desired, second end 1364 of inner tube 1358 is moved in an "upward" direction toward header or carousel 1336, as indicated by directional arrow 1341, away from stent 100, causing the bulbous second end 1364 of inner tube 1358 to come into contact with the fingers formed on second end 1363 of outer tube 1356. Bulbous second end 1364 of inner tube 1358 radially deploys and/or spreads out the fingers formed on second end 1363 of outer tube 1356 until the fingers grab onto or abut against the inner diameter of stent 100 as shown in FIG. 13B. In one embodiment, the deployed fingers may slightly expand the inner diameter of stent 100 to increase the friction between stent 100 and stent suspension means 1328 to minimize undesired movement of stent 100.

Figure 13C:
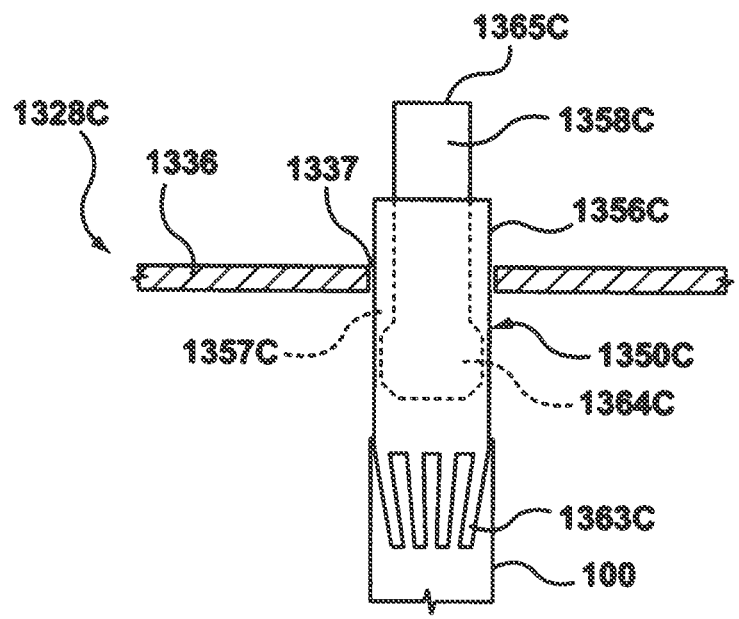
FIGS. 13C-13D illustrate another embodiment of a stent suspension means, which holds or secures the plurality of stents in place during the capillary filling procedure described in FIGS. 4A-7.
Figure 13D:
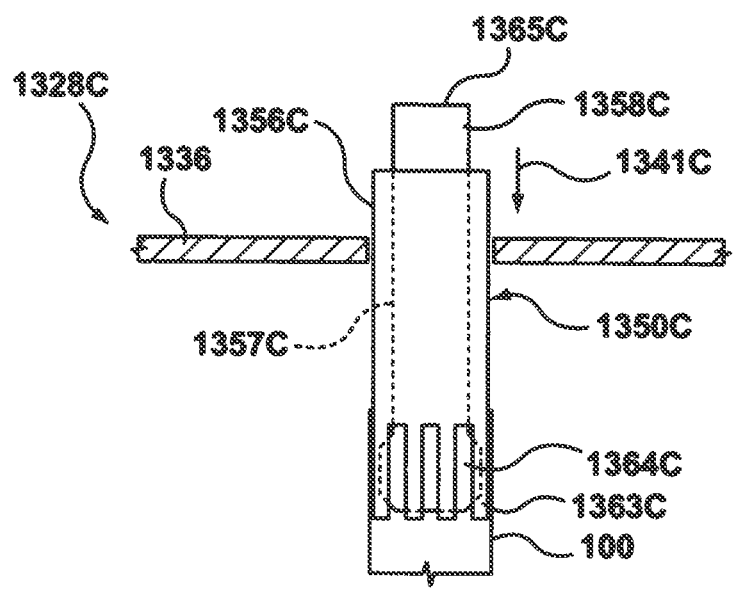

FIGS. 13C-13D illustrate another embodiment of a stent suspension means 1328C that includes header or carousel 1336, a portion of which is shown in the figure, and a mandrel 1350C for holding a stent 100 in place during the capillary filling procedure described with reference to FIGS. 4A-7. Although only one mandrel 1350 is shown, it will be understood by one of ordinary skill in the art that a plurality of mandrels may be coupled to header or carousel 1336 for accommodating a plurality of stents 100. As described with respect to FIG. 13A, header or carousel 1336 is a generally flat sheet-like component having at least one hole or passageway 1337 formed there through to allow for passage of a portion of mandrel 1350C. Mandrel 1350C includes two concentric tubes or shafts that extend through passageway 1337C of header or carousel 1336C, an outer tube 1356C and an inner tube 1358C slidably mounted to extend through a lumen 1357C defined by outer tube 1356C. Outer tube 1356C may be a Nitinol tube and a second end 1363C of outer tube 1356C includes a plurality of fingers, similar to a collet. In this embodiment, unlike the embodiment of FIGS. 13A-B, the fingers formed on the second end 1363C of outer tube 1356C may be initially curved or bent radially inward toward inner tube 1358C. At least a second end 1364C of inner tube 1358C has a diameter only slightly less than the inner diameter of outer tube 1356C. Inner tube 1358C may be pushed or pulled relative to outer tube 1356C to radially deploy the fingers formed on second end 1363C of outer tube 1356C. In operation, second end 1365C of inner tube 1358C is positioned such that the second end 1364C of inner tube 1358C is not in contact with the fingers formed on second end 1363C of outer tube 1356C as shown in FIG. 13C. Once stent 100 is in position as desired, second end 1364C of inner tube 1358C is moved in a "downward" direction toward header or carousel 1336, as indicated by directional arrow 1341C, towards stent 100, causing the second end 1364C of inner tube 1358C to come into contact with the fingers formed on second end 1363C of outer tube 1356C. Second end 1364C of inner tube 1358C straightens and/or spreads out the fingers formed on second end 1363C of outer tube 1356C until the fingers grab onto or abut against the inner diameter of stent 100 as shown in FIG. 13D. In one embodiment, the deployed fingers may slightly expand the inner diameter of stent 100 to increase the friction between stent 100 and stent suspension means 1328C to minimize undesired movement of stent 100.

Figure 14A:
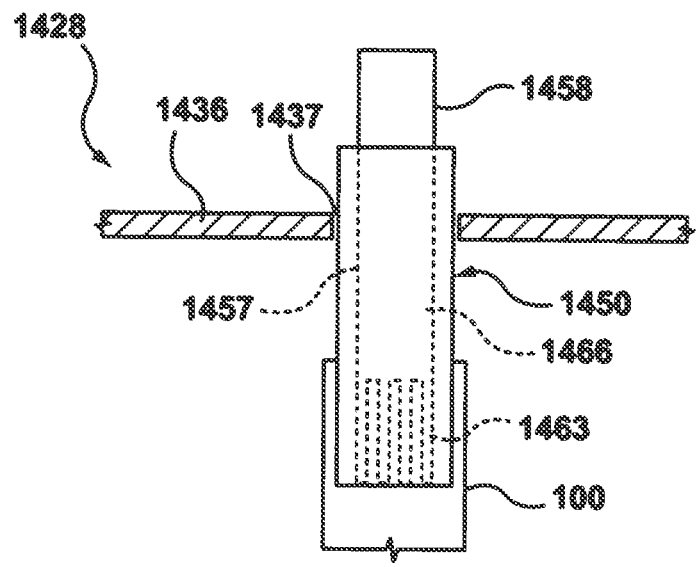
FIGS. 14A-14B illustrate another embodiment of a stent suspension means, which holds or secures the plurality of stents in place during the capillary filling procedure described in FIGS. 4A-7.
Figure 14B:
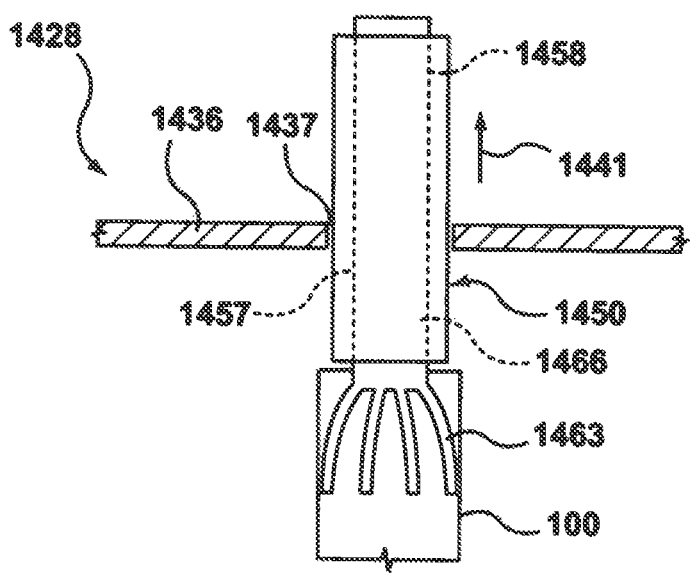

FIGS. 14A-14B illustrate another embodiment of a stent suspension means 1428 includes a header or carousel 1436, a portion of which is shown in the figure, and a mandrel 1450 for holding a stent 100 in place during the capillary filling procedure described with reference to FIGS. 4A-7. Although only one mandrel 1450 is shown, it will be understood by one of ordinary skill in the art that a plurality of mandrels may be coupled or attached to header or carousel 1436 for accommodating a plurality of stents 100. Header or carousel 1436 is a generally flat sheet-like component having at least one hole or passageway 1437 formed there through to allow for passage of a portion of mandrel 1450. Mandrel 1450 includes two concentric tubes or shafts that extend through passageway 14374 of header or carousel 1436, a retractable outer tube 1466 and an inner tube 1458 slidably mounted to extend through a lumen 1457 defined by outer tube 1466. Inner tube 1458 may be a Nitinol tube, and a second end 1463 of inner tube 1458 includes a plurality of self-expanding fingers, similar to a collet. Outer tube 1466 has an outer diameter less than the inner diameter of stent 100. In operation, stent 100 is positioned over outer tube 1466, which radially constrains the fingers formed on second end 1463 of mandrel 1450 as shown in FIG. 14A. Outer tube 1466 may be moved in an "upward" direction toward header or carousel 1436, as indicated by directional arrow 1441, away from stent 100, to expose the fingers formed on second end 1463 of mandrel 1450, causing the fingers formed on second end 1463 of mandrel 1450 to self-expand and radially deploy until the fingers grab onto or abut against the inner diameter of stent 100 as shown in FIG. 14B. In one embodiment, the deployed fingers may slightly expand the inner diameter of stent 100 to increase the friction between stent 100 and stent suspension means 1428 to minimize undesired movement of stent 100. When it is desired to retract or radially constrain the fingers formed on second end 1463 of mandrel 1450, outer tube 1466 is moved in a downwards direction to resume the configuration shown in FIG. 14A.

Figure 15A:
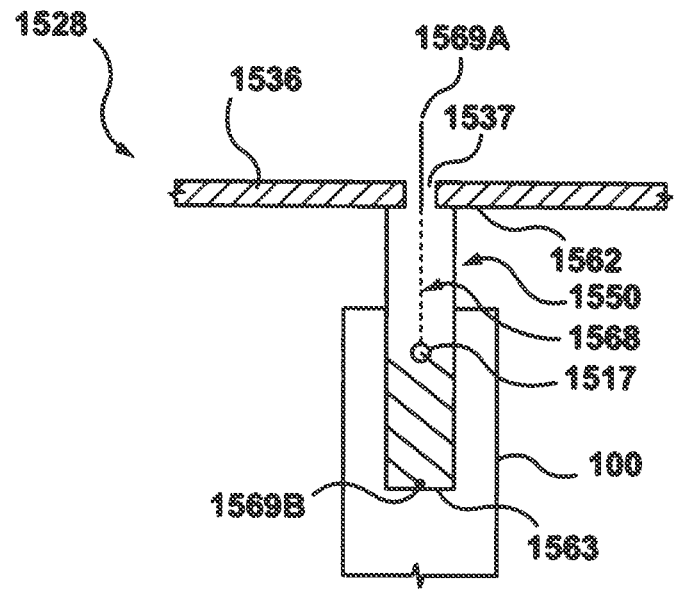
FIGS. 15A-15B illustrate another embodiment of a stent suspension means, which holds or secures the plurality of stents in place during the capillary filling procedure described in FIGS. 4A-7.
Figure 15B:
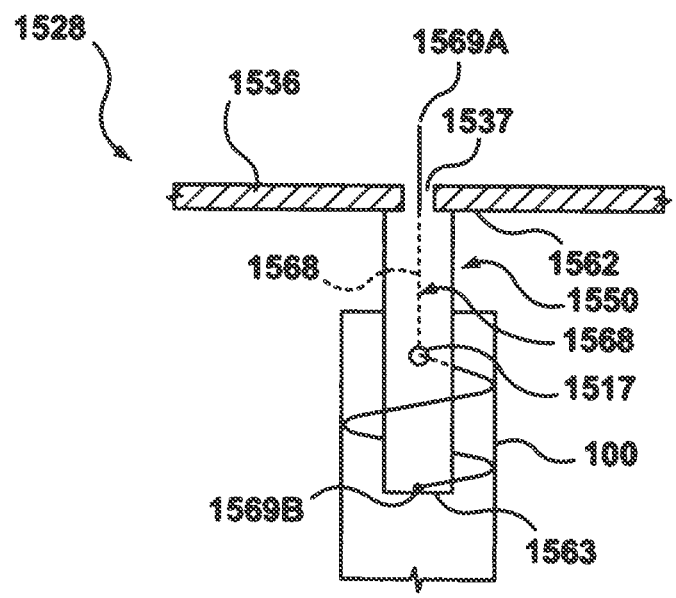

FIGS. 15A-15B illustrate another embodiment of a stent suspension means 1528 includes a header or carousel 1536, a portion of which is shown in the figure, and a mandrel 1550 for holding a stent 100 in place during the capillary filling procedure described with reference to FIGS. 4A-7. Although only one mandrel 1550 is shown, it will be understood by one of ordinary skill in the art that a plurality of mandrels may be coupled or attached to header or carousel 1536 for accommodating a plurality of stents 100. Header or carousel 1536 is a generally flat sheet-like component having at least one hole or passageway 1537 formed there through. Mandrel 1550 is a hollow shaft or tube having a hole 1517 formed in a sidewall thereof, and a first end 1562 of mandrel 1550 is coupled to header or carousel 1536. A Nitinol wire 1568 having a first end 1569A and a second end 1569B extends through passageway 1537 of header 1536, through the lumen of mandrel 1550, exits out of hole 1517 formed in the mandrel, and tightly wraps or winds around the exterior surface of mandrel 1550 as shown in FIG. 15A. Second end 1569B is coupled to a second end 1563 of mandrel 1550. In operation, stent 100 is positioned over mandrel 1550. Once stent 100 is in position as desired, tension on wire 1568 is released, causing helical Nitinol wire 1568 to self-expand and radially deploy to its shape set configuration in which the helical windings thereof grab onto or abut against the inner diameter of stent 100 as shown in FIG. 15B. Wire 1568 may be pulled back to its original position shown in FIG. 15A by retracting the wire back into the lumen of mandrel 1550, thereby reducing the diameter of the helical windings of wire 1568. In one embodiment, the deployed helical windings of helical Nitinol wire 1568 may slightly expand the inner diameter of stent 100 to increase the friction between stent 100 and stent suspension means 1528 to minimize undesired movement of stent 100.

Figure 16:
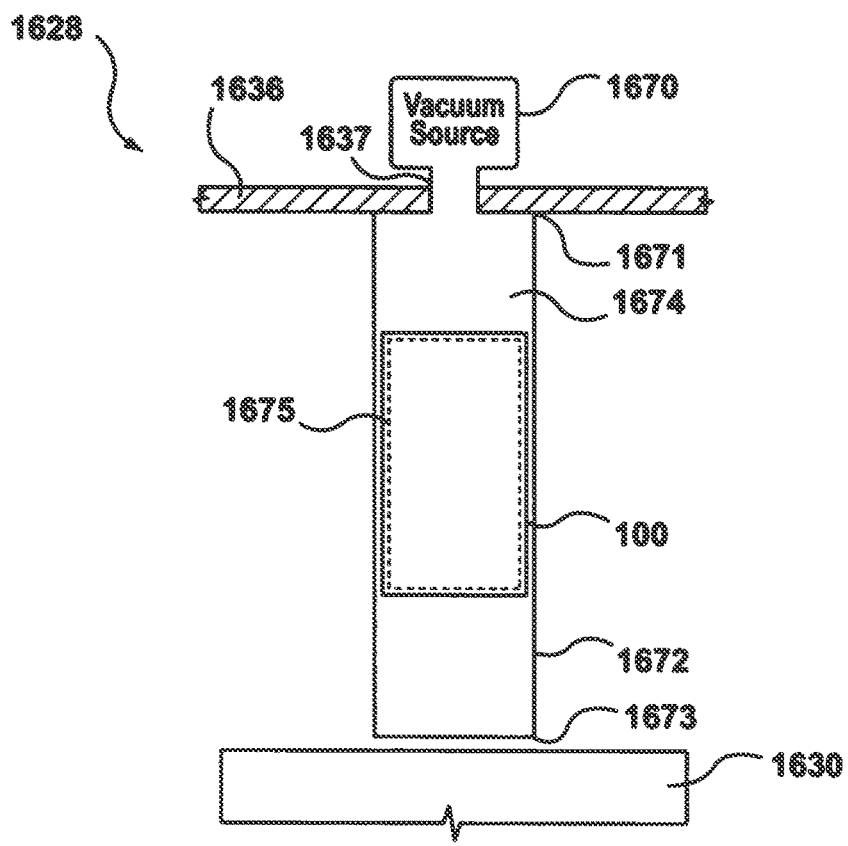
FIG. 16 illustrates another embodiment of a stent suspension means, which holds or secures the plurality of stents in place during the capillary filling procedure described in FIGS. 4A-7.

FIG. 16 illustrates another embodiment of a stent suspension means 1628 includes a header or carousel 1636, a portion of which is shown in the figure, and an elongated tubular component 1672 for holding a stent 100 in place during the capillary filling procedure described with reference to FIGS. 4A-7. Although only one tubular component 1672 is shown, it will be understood by one of ordinary skill in the art that a plurality of tubular components may be coupled to header or carousel 1636 for accommodating a plurality of stents 100. Header or carousel 1636 is a generally flat sheet-like component. A lumen or passageway 1674 of tubular component 1672 is slightly greater than the outer diameter of stent 100. A first open end 1671 of tubular component 1672 is coupled or attached to header or carousel 1636, and a second open end 1673 of tubular component 1672 is positioned adjacent to or proximate to a wicking means 1630. Lumen 1674 of tubular component 1672 is in fluid communication with a vacuum source 1670. In operation, stent 100 is within the lumen of tubular component 1672, and vacuum source 1670 is controlled to lower or raise the stent towards or away from wicking means 1630 as desired. For example, after stent 100 is filled, suction may be applied from vacuum source 1670 in order to retract stent 100 away from wicking means 1630. In one embodiment, a cylindrical plug 1675 may be positioned within the inner diameter of stent 100 to minimize air passage through stent 100 when vacuum source 1670 is used to control the longitudinal position of the stent within tubular component 1672.

Figure 17:
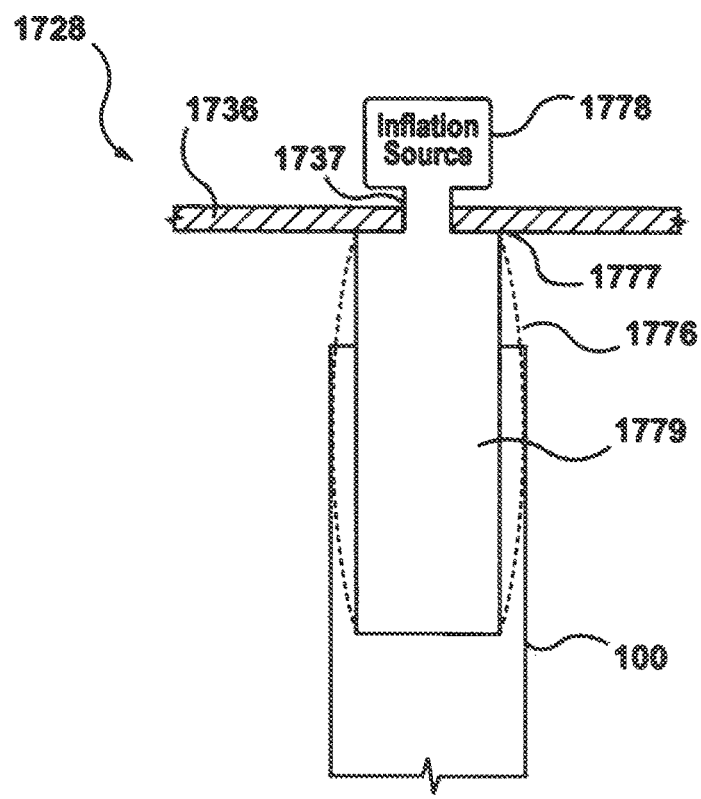
FIG. 17 illustrates another embodiment of a stent suspension means, which holds or secures the plurality of stents in place during the capillary filling procedure described in FIGS. 4A-7.

FIG. 17 illustrates another embodiment of a stent suspension means 1728 that includes a header or carousel 1736, a portion of which is shown in the figure, and an inflatable balloon 1776 for holding a stent 100 in place during the capillary filling procedure described with reference to FIGS. 4A-7. Although only one balloon 1776 is shown, it will be understood by one of ordinary skill in the art that a plurality of balloons may be coupled to header or carousel 1736 for accommodating a plurality of stents 100. Header or carousel 1736 is a generally flat sheet-like component and a first end 1777 of balloon 1776 is coupled or attached to header or carousel 1736. Balloon 1776 may be a cylindrical or tubular shaped balloon, and an interior 1779 of balloon 1776 is in fluid communication with an inflation source 1778. Prior to inflation, balloon 1776 has an outer diameter that fits within stent 100. Once stent 100 is in position as desired, balloon 1776 is inflated via inflation source 1778. Balloon 1776 inflates or expands until its exterior surface abuts against or is in opposition with the inner diameter of stent 100 as shown in phantom in FIG. 17. The inflated balloon 1776 thus grabs onto the inner diameter of stent 100, and in one embodiment, may slightly expand the inner diameter of stent 100 to increase friction between stent 100 and stent suspension means 1728 to minimize undesired movement of stent 100. Exemplary materials for balloon 1776 include but are not limited to Polyethylene terephthalate (PET), polyethylene (PE), nylon, nylon blends, polyurethanes, polyesters, Hytrel, PEBA resins, and PEBAX.

Figure 18A:
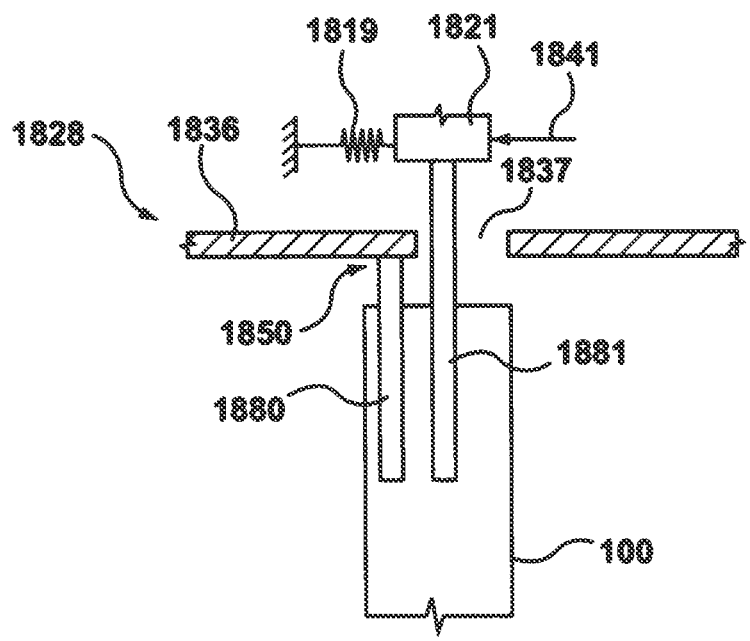
FIGS. 18A-18B illustrate another embodiment of a stent suspension means, which holds or secures the plurality of stents in place during the capillary filling procedure described in FIGS. 4A-7.
Figure 18B:
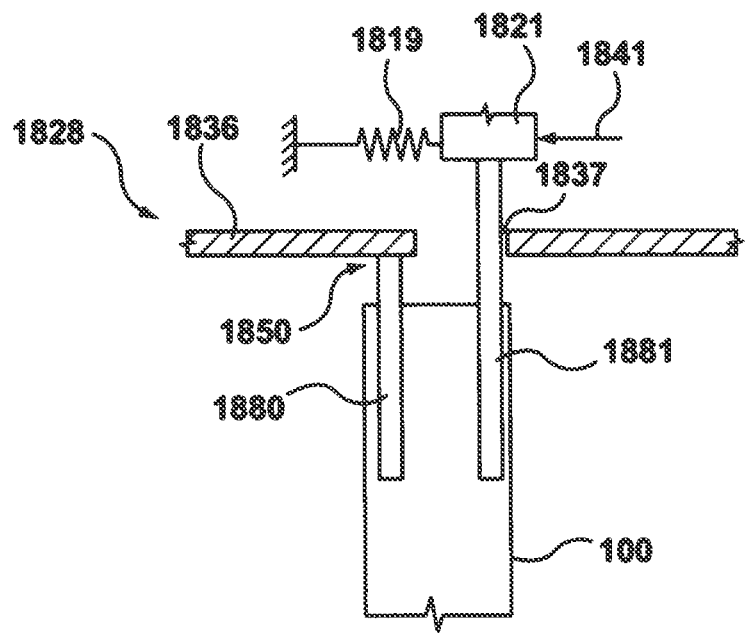

FIGS. 18A-18B illustrate another embodiment of a stent suspension means 1828 that includes a header or carousel 1836, a portion of which is shown in the figure, and a mandrel 1850 for holding a stent 100 in place during the capillary filling procedure described with reference to FIGS. 4A-7. Although only one mandrel 1850 is shown, it will be understood by one of ordinary skill in the art that a plurality of mandrels may be coupled to header or carousel 1836 for accommodating a plurality of stents 100. Header or carousel 1836 is a generally flat sheet-like component having at least one slot or passageway 1837 formed there through to allow for passage of a portion of mandrel 1850. Mandrel 1850 includes two adjacent pins or shafts, a first stationary pin 1880 coupled to header or carousel 1836 and a second movable pin 1881 which extends through slot 1837 of header or carousel 1836. Second movable pin 1881 may be laterally shifted or moved to selectively retain stent 100. More particularly, second movable pin 1881 is mounted in a block 1821 above the header carousel 1836 with a compression spring 1819 extending between the block and the header. Compression spring 1819 provides a force that tends to move the second pin 1881 away from the stationary pin 1880, as shown in FIG. 18B. In operation, a force 1841 is externally applied, i.e., applied by an operator pressing on block 1821, to compress spring 1819 and thereby shift or move second movable pin 1881 within slot 1837 so that it is relatively close to stationary pin 1880 as shown in FIG. 18A. Stent 100 is then placed over both stationary pin 1880 and movable pin 1881, with the first stationary pin 1880 in contact with the inner surface or diameter of stent 100. Once stent 100 is in position as desired, force 1841 is removed and spring 1819 resumes its natural configuration that laterally moves second movable pin 1881 away from stationary pint 1880 as shown in FIG. 18B. When moved apart from stationary pin 1880, movable pin 1881 comes into contact with the inner surface or diameter of stent 100 and collectively pins 1880, 1881 abut against the inner diameter of stent 100 in an interference or friction fit. Pins 1880, 1881 contact the inner diameter of stent 100 at opposing locations.

Figure 18C:
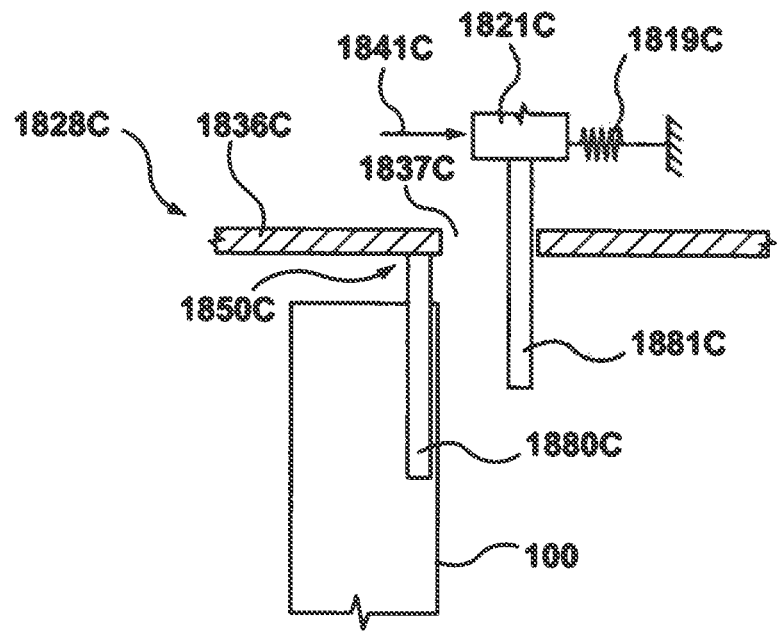
FIGS. 18C-18D illustrate another embodiment of a stent suspension means, which holds or secures the plurality of stents in place during the capillary filling procedure described in FIGS. 4A-7.
Figure 18D:
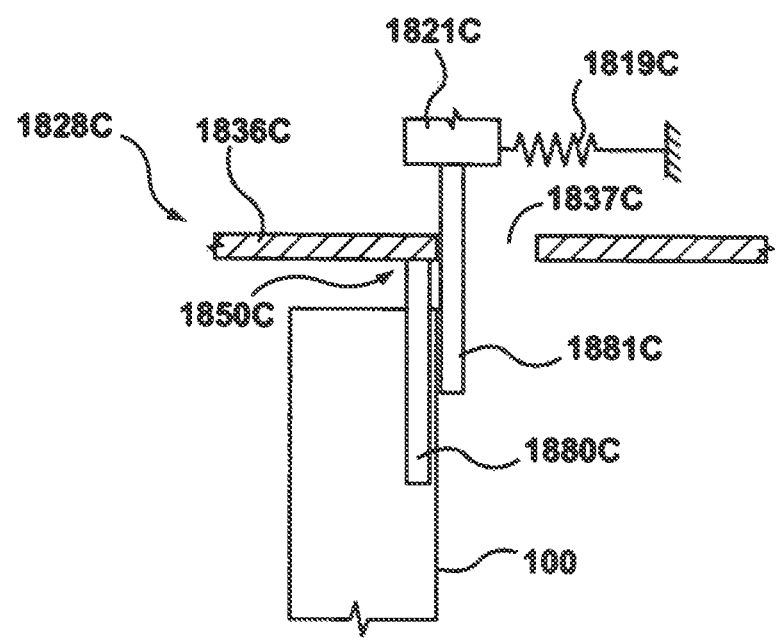

FIGS. 18C-18D illustrate another embodiment of a stent suspension means 1828C that includes a header or carousel 1836C, a portion of which is shown in the figure, and a mandrel 1850C for holding a stent 100 in place during the capillary filling procedure described with reference to FIGS. 4A-7. Although only one mandrel 1850C is shown, it will be understood by one of ordinary skill in the art that a plurality of mandrels may be coupled to header or carousel 1836 for accommodating a plurality of stents 100. Header or carousel 1836C is a generally flat sheet-like component having at least one slot or passageway 1837C formed there through to allow for passage of a portion of mandrel 1850C. Mandrel 1850C includes two adjacent pins or shafts, a first stationary pin 1880C coupled to header or carousel 1836C and a second movable pin 1881C which extends through slot 1837C of header or carousel 1836C. Second movable pin 1881C may be laterally shifted or moved to selectively retain stent 100. More particularly, second movable pin 1881C is mounted in a block 1821C above the header carousel 1836C with a compression spring 1819C extending between the block and the header. Compression spring 1819C provides a force that tends to move the second pin 1881C toward the stationary pin 1880C, as shown in FIG. 18D. In operation, a force 1841C is externally applied, i.e., applied by an operator pressing on block 1821C, to compress spring 1819C and thereby shift or move second movable pin 1881C within slot 1837C so that it is relatively spaced apart from stationary pin 1880C as shown in FIG. 18C. Stent 100 is then placed between stationary pin 1880C and movable pin 1881, with the first stationary pin 1880C in contact with the inner surface or diameter of stent 100. Once stent 100 is in position as desired, force 1841C is removed and spring 1819C resumes its natural configuration that laterally moves second pin 1881C toward stationary pint 1880C as shown in FIG. 18D. When moved towards stationary pin 1880C, movable pin 1881C comes into contact with the an outer surface or diameter of stent 100 such that a sidewall of stent 100 is effectively sandwiched or captured between pins 1880C, 1881C.

FIGS. 19A-19D illustrate another embodiment of a stent suspension means 1928 that includes a header or carousel 1936, a portion of which is shown in the figure, and a mandrel 1950 for holding a stent 100 in place during the capillary filling procedure described with reference to FIGS. 4A-7. Although only one mandrel 1950 is shown, it will be understood by one of ordinary skill in the art that a plurality of mandrels may be coupled to header or carousel 1936 for accommodating a plurality of stents 100. Header or carousel 1936 is a generally flat sheet-like component having at least one slot or passageway 1937 formed there through to allow for passage of a portion of mandrel 1950 and a collet 1982. Collet 1982 has a tapered or frustoconical outer surface and a lumen or hole 1925 extending there through, which is sized slightly larger than an outer diameter of stent 100. Multiple cuts 1923 are formed at one end of collet, in the sidewall thereof, to form jaws 1982A, 1982B, 1983C. Mandrel 1950, having an outer diameter slightly smaller than the inner diameter of stent 100, extends through lumen 1925 of collet 1982. In operation, stent 100 is placed over mandrel 1950 and within collet 1982 as shown in FIGS. 19A-19B. Cuts 1923 in collet 1982 allow adjacent jaws of the collet to spread apart. Once stent 100 is in position as desired, collet 1982 may be moved in an "upward" direction toward header or carousel 1936, as indicated by directional arrow 1441, away from stent 100, until the outer surface of the collet contacts the edge of passageway 1937 of header 1936. When the outer diameter of collet 1982 is greater than the diameter of passageway 1937, passageway 1937 applies an inward radial force onto the collet and squeezes or moves jaws 1982A, 1982B, 1983C together as shown in FIGS. 19C-19D. An inner diameter of lumen 1925 of collet 1982 is reduced to effectively clamp or capture stent 100 between the inner surface of collet 1982 and the exterior surface of mandrel 1950.

Figure 20:
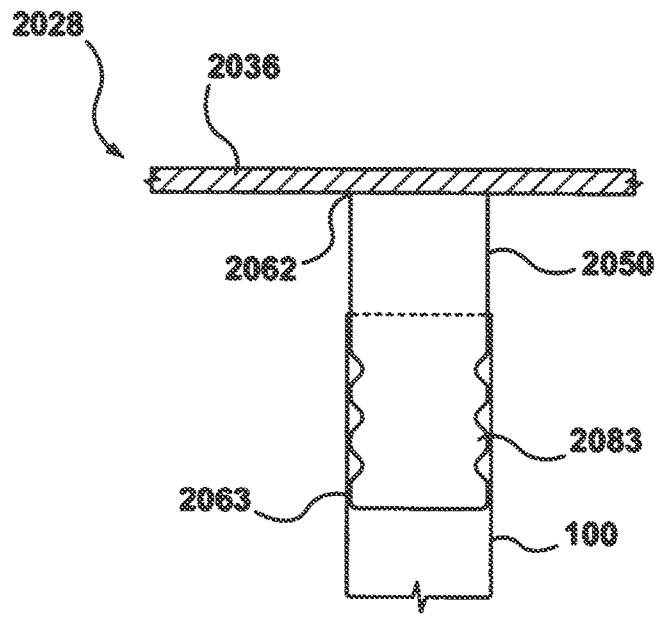
FIG. 20 illustrates another embodiment of a stent suspension means, which holds or secures the plurality of stents in place during the capillary filling procedure described in FIGS. 4A-7.

FIG. 20 illustrates another embodiment of a stent suspension means 2028 that includes a header or carousel 2036, a portion of which is shown in the figure, and a mandrel 2050 for holding a stent 100 in place during the capillary filling procedure described with reference to FIGS. 4A-7. Although only one mandrel 2050 is shown, it will be understood by one of ordinary skill in the art that a plurality of mandrels may be coupled to header or carousel 2036 for accommodating a plurality of stents 100. Header or carousel 2036 is a generally flat sheet-like component and a first end 2062 of mandrel 2050 is coupled to header or carousel 2036. Mandrel 2050 includes a wavy or bumpy exterior surface adjacent to at least a second end 2063. The wavy or bumpy exterior surface of mandrel 2050 is formed via circumferential ribs or bands 2083 having an increased outer diameter relative to the remainder of mandrel 2050. The wavy or bumpy exterior surface of mandrel 2050 abuts against the inner diameter of stent 100 in an interference or friction fit. Mandrel 2050 may be formed from 3 series stainless steel, or other material that is not prone to oxidation or corrosion, and is not dissolvable and unaffected by harsh chemicals. In another embodiment (not shown), mandrel 2050 may have a straight exterior surface that abuts against the inner diameter of stent 100 in an interference or friction fit and the tip of the slip-fit mandrel may include a chamfer, a taper, or may be substantially flat for an improved fit with the stent. In yet another embodiment (not shown), rather than a tubular shaft or rod as a mandrel, the stent suspension means may consist of one or more springs or coiled wires that are offset from each other and collectively form a tubular mandrel. The springs or coiled wires that make up a tubular mandrel abut against the inner diameter of stent 100 in an interference or friction fit.

Figures 21, 21A:
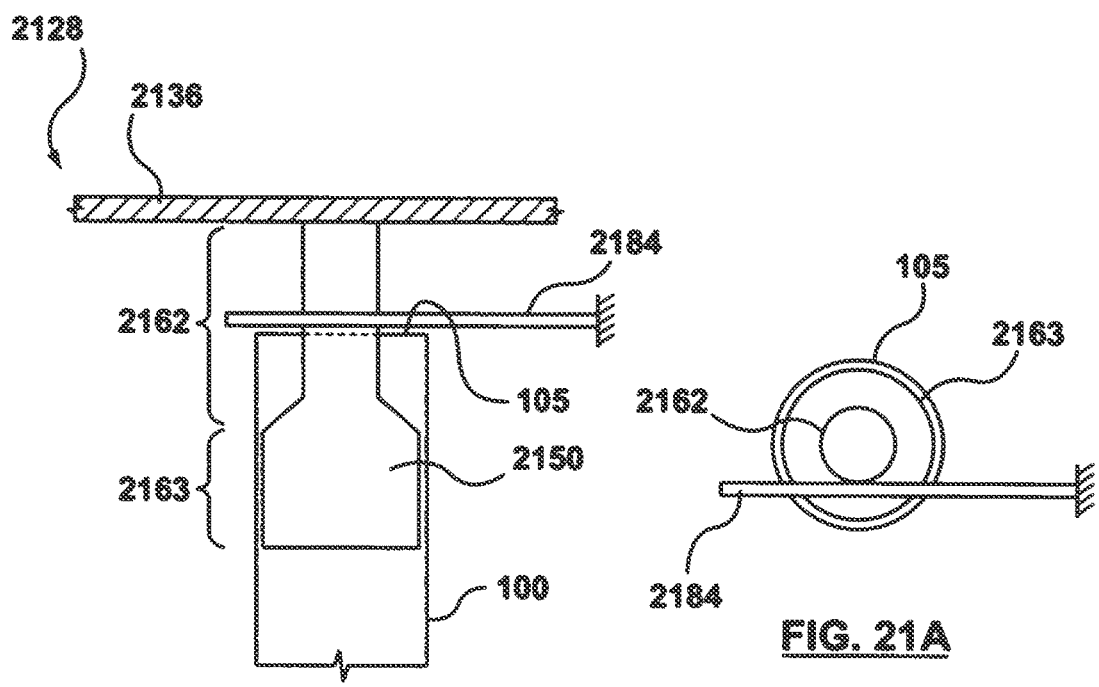
FIGS. 21-21A illustrates another embodiment of a stent suspension means, which holds or secures the plurality of stents in place during the capillary filling procedure described in FIGS. 4A-7.

FIGS. 21-21A illustrate another embodiment of a stent suspension means 2128 that includes a header or carousel 2136, a portion of which is shown in the figure, and a mandrel 2150 for holding a stent 100 in place during the capillary filling procedure described with reference to FIGS. 4A-7. FIG. 21A is a top view of FIG. 21 with header or carousel 2136 removed. Although only one mandrel 2150 is shown, it will be understood by one of ordinary skill in the art that a plurality of mandrels may be coupled to header or carousel 2136 for accommodating a plurality of stents 100. Header or carousel 2136 is a generally flat sheet-like component and a first end portion 2162 of mandrel 2150 is coupled to header or carousel 2136. First end portion 2162 of mandrel 2150 has a smaller outer diameter than a second end portion 2163 of mandrel 2150. The outer diameter of second end portion 2163 of mandrel 2150 abuts against the inner diameter of stent 100 in an interference or friction fit. To position stent 100 over mandrel 2150, stent 100 is slid up mandrel 2150 until end 105 of stent 100 is past wider second end portion 2163 of mandrel 2150 and is positioned over narrower first end portion 2162 of mandrel 2150. A stationary cantilevered spring leaf or arm 2184 extends adjacent to first end portion 2162 of mandrel 2150 and contacts and abuts against end 105 of stent 100. When stent 100 is lowered into wicking component 430 within second chamber 424, the stent may experience an upward force due to the interaction of the stent with the wicking component 430 that may cause the stent to unintentionally slip up mandrel 2150. Spring arm 2184 counters any unintentional upward forces that result due to the interaction of the stent with the wicking component 430 by exerting a downward force onto stent 100 if spring arm 2184 is deflected from its neutral position shown in FIG. 21. Spring arm 2184 thus acts to press stent 100 into the wicking component for more uniform loading during the filling process when a plurality of stents are present.

FIGS. 22A-22C illustrate another embodiment of a stent suspension means 2228 that includes a header or carousel 2236, a portion of which is shown in the figure, and a mandrel 2250 for holding a stent 100 in place during the capillary filling procedure described with reference to FIGS. 4A-7. FIG. 22C is a sectional view taken along line C-C of FIG. 22B. Although only one mandrel 2250 is shown, it will be understood by one of ordinary skill in the art that a plurality of mandrels may be coupled to header or carousel 2236 for accommodating a plurality of stents 100. Header or carousel 2236 is a generally flat sheet-like component and a first end 2262 of mandrel 2250 is coupled to header or carousel 2236. In operation, stent 100 is placed over mandrel 2250 as shown in FIG. 22A. Once stent 100 is in position as desired, a spring-loaded, movable arm 2285 pushes stent 100 against mandrel 2250 as shown in FIGS. 22B and 22C to effectively sandwich or capture stent 100 between arm 2285 and the exterior surface of mandrel 2250. Arm 2285 rotates or moves via a spring 2286 and a pivot 2287.

Means for Wicking Fluid Drug Formulation

FIGS. 23-33 illustrate several embodiments of wicking means 430, which is in contact with fluid drug formulation 432 to control transfer of the fluid drug formulation 432 into lumen 103 of hollow wire 102 during the capillary filling procedure as described in FIGS. 4A-7. "Wicking means" as used herein refers to a medium or component that acts or functions to move or convey, or acts or functions to assist in the movement of, the fluid drug formulation 432 by capillary action from within second or lower chamber 424 into lumen 103 of hollow wire 102. In addition to controlling transfer of the fluid drug formulation, in some embodiments hereof, wicking means 430 also removes excess fluid drug formulation from the exterior surfaces of hollow wire 102 of stent 100 when stent 100 is retracted out of the wicking means. When wicking means 430 performs this excess removal function, an additional processing or cleaning step is not required to make stents 100 free or substantially free of drug residue on the exterior surfaces of hollow wire 102. Wicking means 430 preferably has several characteristics or properties, including that is does not degrade or add contaminants into fluid drug formulation 432, that it is inert in fluid drug formulation 432, that it does not cause a phase separation within fluid drug formulation 432, and that it is usable and/or stable for several days or weeks.

As previously mentioned, in one embodiment wicking means 430 is an open-celled polyurethane sponge. Several characteristics or properties may be varied to improve the sponge's effectiveness to further reduce fill weight variability, including the polymer material's chemical structure, the hydrophilicity of the sponge, the pore size of the sponge, the density of the sponge, the compression modulus of the sponge, and/or the shape or dimensions of the sponge. For example, hydrophilicity and pore size have a direct correlation with capillary action and therefore fluid affinity. Thus, optimization of these properties allows the sponge to better clean the exterior surfaces of hollow wire 102 of stent 100. In addition, the compression modulus of the sponge allows for a controlled amount of the stent to come into contact with the wicking means. An optimized amount of deformation permits the sponge to come into contact with side holes 104 of stent 100 while limiting the amount of exterior surface of hollow wire 102 of stent 100 that comes into contact with the fluid drug formulation.

Figure 23A:
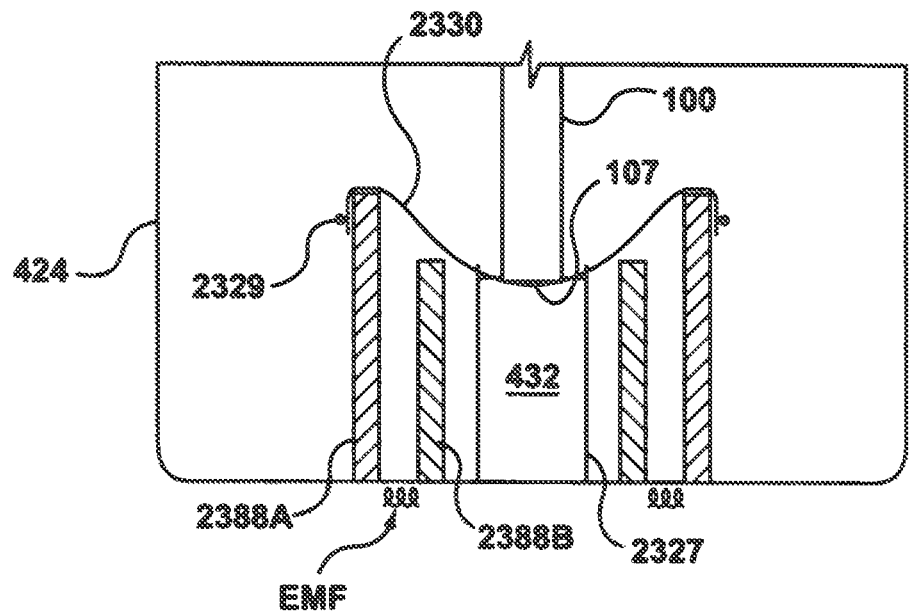
FIGS. 23A-B illustrate an embodiment of a wicking means, which controls transfer of a fluid drug formulation to a stent during the capillary filling procedure described in FIGS. 4A-7.
Figure 23B:
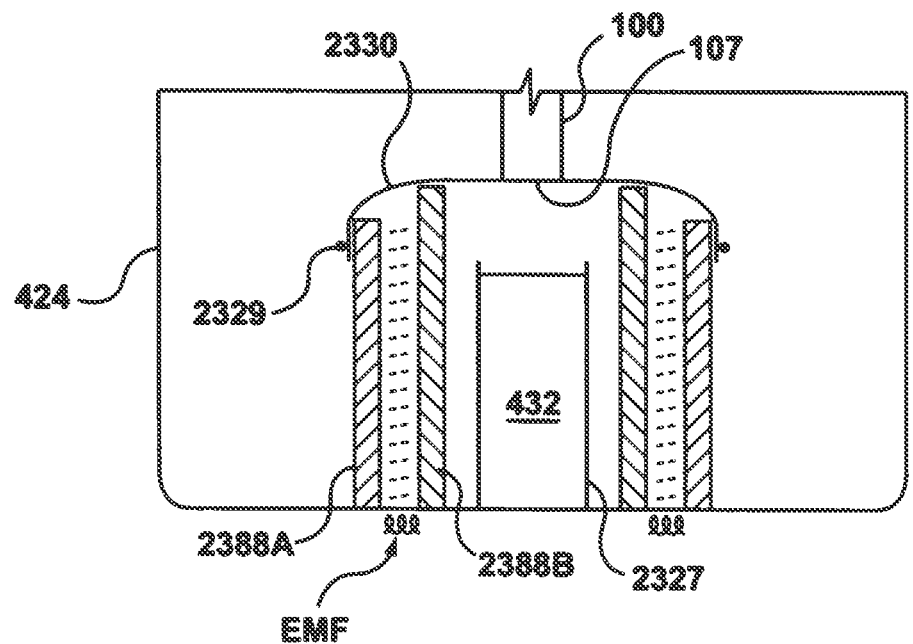

As an alternative to a sponge wicking means, the wicking means may be an intermediate surface or component between the stents and the fluid drug formulation 432 that makes contact with fluid drug formulation 432 to control transfer of the fluid drug formulation 432 into lumen 103 of hollow wire 102 during the capillary filling procedure as described in FIGS. 4A-7. For illustrative purposes, stents 100 are represented as straight tubular structures in FIGS. 23-33 although it will be understood by one of ordinary skill in the art that stents 100 are a hollow wire shaped into a desired stent pattern as discussed with reference to FIG. 1. For example, FIG. 23 illustrates a portion of lower or second chamber 424 having a portion of a stent 100 lowered to contact a wicking means 2330. Wicking means 2330 is a deformable membrane or sheet that is held over a layer of fluid drug formulation 432 held within a container 2327 second chamber 424. In one embodiment, wicking means 2330 is a continuous filament polyester fiber sheet of material, or a purity wipe. The position or configuration of wicking means 2330 is controlled via two concentric tubes, a first or outer stationary tube 2388A and a second or inner movable tube 2388B. Tubes 2388A, 2388B may be cylindrical or rectangular in cross-section. Wicking means 2330 extends or drapes over a top of outer stationary tube 2388A and is held in place over outer stationary tube 2388A via an O-ring 2329 formed of an inert substance such as Teflon. In another embodiment, wicking means 2330 may be held in place over outer stationary tube 2388A via a clamp. In operation, wicking means 2330 is draped over outer stationary tube 2388A such that a center of the wicking means sages and contacts fluid drug formulation 432 held within container 2327 as shown in FIG. 23A. Wicking means 2330 thus becomes wetted with fluid drug formulation 432 in a first configuration such that when end 107 of stent 100 is placed into contact with wicking means 2330, fluid drug formulation 432 fills or is wicked up into lumen 103 of hollow wire 102 via capillary action. When filling is complete, stent 100 is raised in conjunction with inner movable tube 2388B. Inner movable tube 2388B is raised via an applied electromotive force via an EMF source, and pushes wicking means 2330 upwards into a second configuration in which the deformable sheet is not in contact with fluid drug formulation 432 held within container 2327 as shown in FIG. 23B. The deformable sheet or membrane of wicking means 2330 becomes taut and allows excess fluid drug formulation on exterior surfaces of hollow wire 102 of stent 100 to drain from the stent onto the wicking means. Once the excess fluid drug formulation 432 has drained, the electromotive force is removed and inner movable tube 2388B is lowered to the original position of FIG. 23A.

Figure 24:
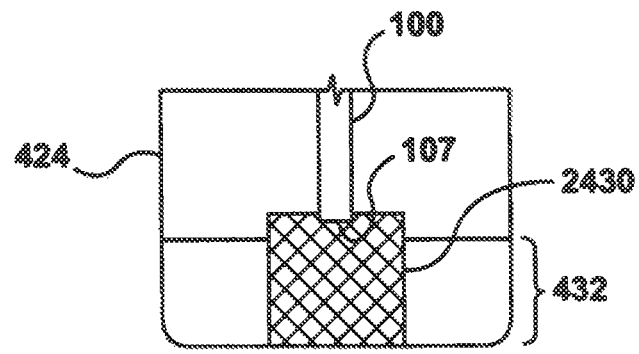
FIG. 24 illustrates another embodiment of a wicking means, which controls transfer of a fluid drug formulation to a stent during the capillary filling procedure described in FIGS. 4A-7.

FIG. 24 is another embodiment of the wicking means as an intermediate surface or component that is in contact with fluid drug formulation 432 to control transfer of the fluid drug formulation 432 into lumen 103 of hollow wire 102 during the capillary filling procedure as described in FIGS. 4A-7. FIG. 24 illustrates a portion of lower or second chamber 424 having a portion of a stent 100 lowered to contact a wicking means 2430. Wicking means 2430 is mesh material positioned within a layer of fluid drug formulation 432 contained within second chamber 424. When end 107 of stent 100 is placed into contact with wicking means 2430, the mesh material deforms or buckles in order to connect and allow contact between stent 100 and the layer of fluid drug formulation 432. After stents 100 have been filled, stents 100 are retracted from contact with wicking means 2430. During retraction of stents 100, the mesh material of wicking means 2430 returns to its original shape and pulls or removes excess fluid drug formulation from the exterior surfaces of stents 100. Exemplary materials for the mesh material of wicking means 2430 include but are not limited to nylon, polyester, polypropylene, or rubber.

Figure 25:
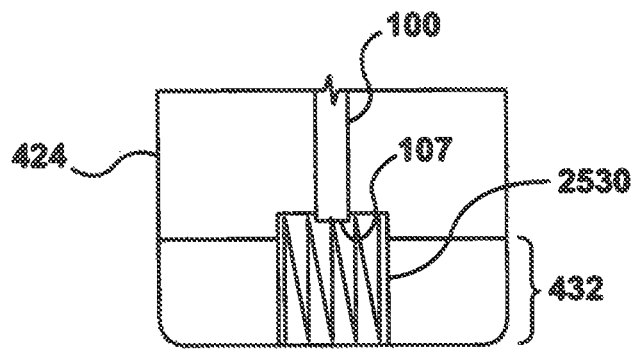
FIG. 25 illustrates another embodiment of a wicking means, which controls transfer of a fluid drug formulation to a stent during the capillary filling procedure described in FIGS. 4A-7.

FIG. 25 is another embodiment of the wicking means as an intermediate surface or component that is in contact with fluid drug formulation 432 to control transfer of the fluid drug formulation 432 into lumen 103 of hollow wire 102 during the capillary filling procedure as described in FIGS. 4A-7. FIG. 25 illustrates a portion of second chamber 424 having a portion of a stent 100 lowered to contact a wicking means 2530. Wicking means 2530 is flocked or textured material positioned within a layer of fluid drug formulation 432 contained within second chamber 424. The flocked or textured sheet of material may be VELCRO, cotton, cellulose, polymer foam, porous polymer blocks, or polymer fibers, and/or artificial grass. When end 107 of stent 100 is placed into contact with wicking means 2530, the textured material deforms or buckles in order to connect and allow contact between stent 100 and the layer of fluid drug formulation 432. After stents 100 have been filled, stents 100 are retracted from contacting wicking means 2530. During retraction of stents 100, the textured material of wicking means 2530 returns to its original shape and pulls or removes excess fluid drug formulation from the exterior surfaces of hollow wires 102 of stents 100.

Figure 26:
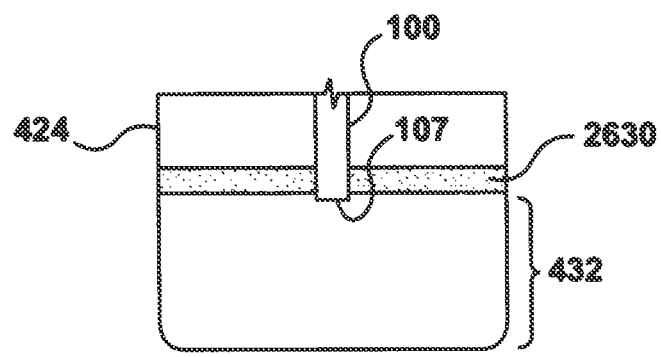
FIG. 26 illustrates another embodiment of a wicking means, which controls transfer of a fluid drug formulation to a stent during the capillary filling procedure described in FIGS. 4A-7.

FIG. 26 is another embodiment of the wicking means as an intermediate surface or component that is in contact with fluid drug formulation 432 to control transfer of the fluid drug formulation 432 into lumen 103 of hollow wire 102 during the capillary filling procedure as described in FIGS. 4A-7. FIG. 26 illustrates a portion of second chamber 424 having a portion of a stent 100 lowered through a wicking means 2630. Wicking means 2630 is a layer of PEG (polyethylene glycol) gel or an immiscible liquid that, when poured into second chamber 424, will separate from and form a top layer on the fluid drug formulation 432. End 107 of stent 100 is placed through wicking means 2630 until the stents 100 are in contact with the layer of fluid drug formulation 432. After stents 100 have been filled, stents 100 are retracted through wicking means 2630. During retraction of stents 100, the cellulose, PEG gel, or immiscible liquid may pull or remove excess fluid drug formulation from the exterior surfaces of stents 100.

Figure 27A:
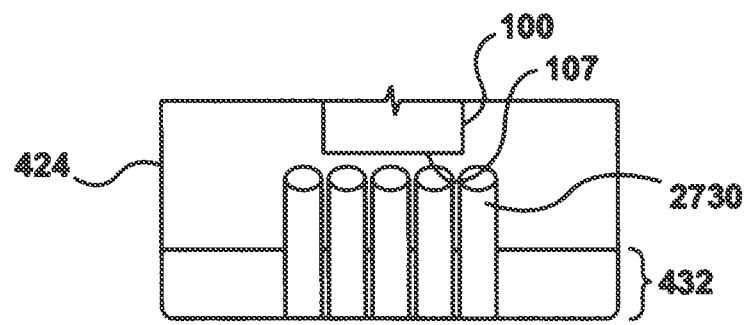
FIGS. 27A-27B illustrate another embodiment of a wicking means, which controls transfer of a fluid drug formulation to a stent during the capillary filling procedure described in FIGS. 4A-7.
Figure 27B:
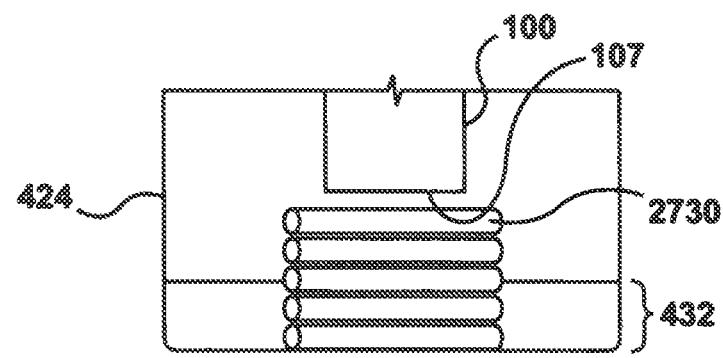

FIGS. 27A-27B illustrates another embodiment of the wicking means that includes an intermediate surface or component that is in contact with fluid drug formulation 432 to control transfer of the fluid drug formulation 432 into lumen 103 of hollow wire 102 during the capillary filling procedure as described in FIGS. 4A-7. FIGS. 27A-27B illustrate a portion of second chamber 424 having a portion of a stent 100 lowered to contact a wicking means 2730. Wicking means 2730 is a plurality of hypotubes or cylindrical microchannels within the layer of fluid drug formulation 432 contained within second chamber 424. The hypotubes are formed out of material that changes orientation when a magnetic or electric field is applied thereto. Stent 100 is placed into the hypotubes of wicking means 2730 until end 107 stent 100 contacts the layer of fluid drug formulation 432. The individual size of the hypotubes, as well as the height of the layer of hypotubes, may vary according to application. During the filling steps, the hypotubes of wicking means 2730 have a first or vertical orientation shown in FIG. 27A which allows fluid drug formulation 432 to pass through the hypotube lumens via capillary action. When fluid drug formulation 432 travels up the hypotubes of wicking means 2730, fluid drug formulation 432 comes into contact with end 107 of stent 100, thereby allowing the lumen 103 of hollow wire 102 of stent 100 to fill via capillary action. Only the open bottoms of the hypotubes are required to be submersed in the fluid drug formulation in order to fill the hypotubes via capillary action. After stents 100 have been filled, an electric or magnetic field is applied to move the hypotubes of wicking means 2730 to a second or horizontal orientation. In the horizontal orientation shown in FIG. 27B, fluid drug formulation 432 does not contact or interact with stent 100 so filling of the stent via capillary action is stopped. Changing the orientation of the hypotubes of wicking means 2730 changes the fluid transfer properties between stent 100 and fluid drug formulation 432. In their vertical orientation, hypotubes readily transfer fluid drug formulation 432 to stent 100 and in their horizontal orientation, capillary action is stopped and fluid affinity is modified to make it easier to clean the exterior surfaces of hollow wire 102 of stent 100.

Figure 28:
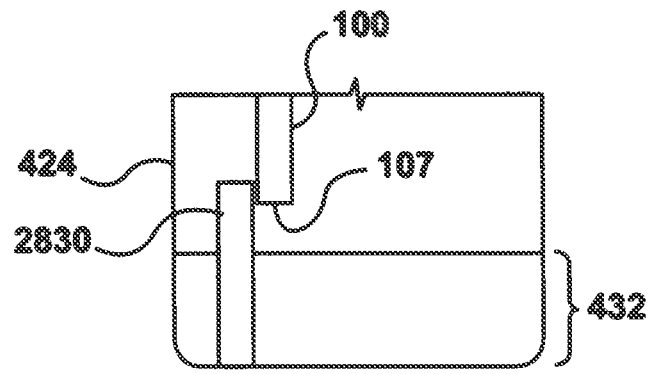
FIG. 28 illustrates another embodiment of a wicking means, which controls transfer of a fluid drug formulation to a stent during the capillary filling procedure described in FIGS. 4A-7.

FIG. 28 is another embodiment of the wicking means as an intermediate surface or component that is in contact with fluid drug formulation 432 to control transfer of the fluid drug formulation 432 into lumen 103 of hollow wire 102 during the capillary filling procedure as described in FIGS. 4A-7. FIG. 28 illustrates a portion of lower or second chamber 424 having a portion of a stent 100 lowered to contact a wicking means 2830. Wicking means 2830 is a cellulose column positioned within and extending past or beyond a layer of fluid drug formulation 432 contained within second chamber 424. End 107 of stent 100 is placed into contact with a side surface of wicking means 2830, which acts as a bridge or conduit between stent 100 and fluid drug formulation 432 to transfer the fluid drug formulation to stent 100. End 107 of stent 100 may alternatively be placed into contact with a top surface of wicking means 2830. The cellulose column minimizes the contact area between stents 100 and fluid drug formulation 432 to control surface energy properties during the filling procedure. As described in more detail here with respect to embodiments in which the stent directly contacts the fluid drug formulation, the surface energy properties of the fluid drug formulation must be controlled in order for the fluid drug formulation to have the greatest affinity for lumen 103 of hollow wire 102 rather than on the exterior surfaces of hollow wire 102 so that the maximum amount of exterior surfaces are kept clean, or substantially free of fluid drug formulation 432, during the filling process.

Figure 29:
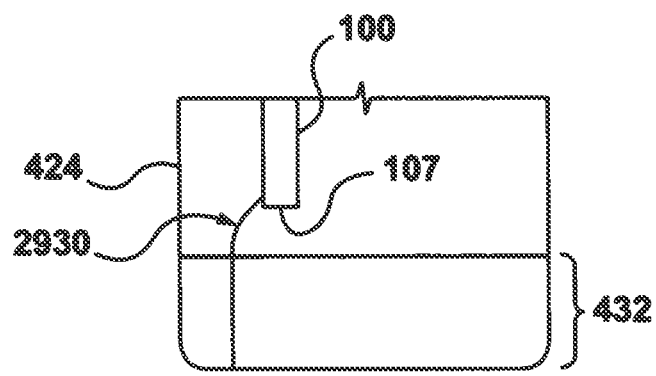
FIG. 29 illustrates another embodiment of a wicking means, which controls transfer of a fluid drug formulation to a stent during the capillary filling procedure described in FIGS. 4A-7.

Similar to FIG. 28, FIG. 29 is another embodiment of the wicking means as an intermediate surface or component that is in contact with fluid drug formulation 432 to control transfer of the fluid drug formulation 432 into lumen 103 of hollow wire 102 during the capillary filling procedure as described in FIGS. 4A-7. FIG. 29 illustrates a portion of lower or second chamber 424 having a portion of a stent 100 lowered to contact a wicking means 2930. Wicking means 2930 is a fiber/filament or a plurality of woven or parallel fibers/filaments positioned within and extending past or beyond a layer of fluid drug formulation 432 contained within second chamber 424. End 107 of stent 100 is placed into contact with a top surface of wicking means 2930 such that wicking means 2930 is in direct contact with an opening or hole 104 formed within wire 102. Wicking means 2930 transfers fluid drug formulation 432 to stent 100 and minimizes the contact area between stents 100 and fluid drug formulation 432 to control surface energy properties during the filling procedure. In another embodiment, wicking means 2930 is a plug of cotton or similar fibrous material.

Figure 30:
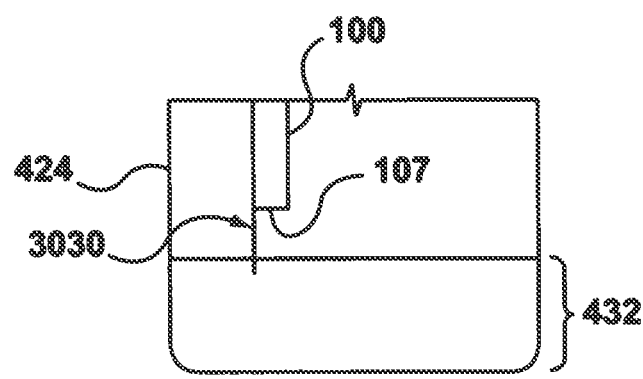
FIG. 30 illustrates another embodiment of a wicking means, which controls transfer of a fluid drug formulation to a stent during the capillary filling procedure described in FIGS. 4A-7.

In FIGS. 28 and 29, the cellulose column or fiber(s) are positioned within and extending past or beyond a layer of fluid drug formulation 432 contained within second chamber 424. Alternatively, as shown in FIG. 30, a wicking means 3030 may extend from end 107 of stent 100 and be dipped or lowered into a layer of fluid drug formulation 432. FIG. 30 illustrates a portion of lower or second chamber 424 having a portion of a stent 100 lowered to contact wicking means 3030. Wicking means 3030 may be a cellulose extension, a fiber/filament, a plurality of woven or parallel fibers/filaments, or a plug of cotton. Wicking means 3030 is coupled to end 107 of stent 100, and stent 100 is lowered within second chamber 424 until a bottom surface of wicking means 3030 is in contact with fluid drug formulation 432. Wicking means 3030 transfers fluid drug formulation 432 to stent 100 and minimizes the contact area between stent 100 and fluid drug formulation 432 to control surface energy properties during the filling procedure.

Figure 31A:
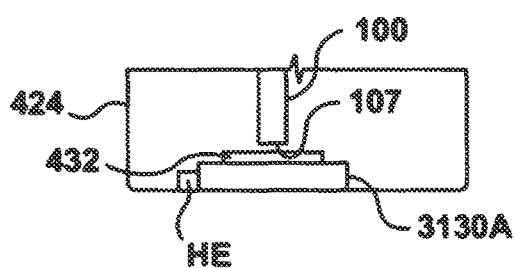
FIGS. 31A-31B illustrate another embodiment of a wicking means, which controls transfer of a fluid drug formulation to a stent during the capillary filling procedure described in FIGS. 4A-7.
Figure 31B:
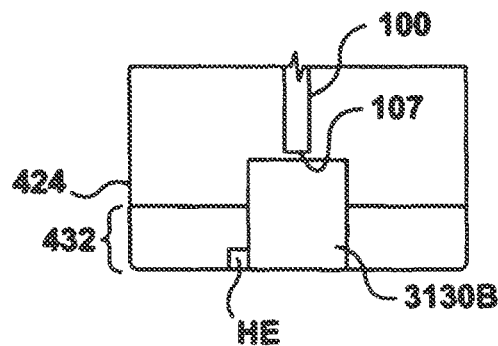

FIGS. 31A-31B illustrate another embodiment of the wicking means in which an intermediate surface or component that is in contact with fluid drug formulation 432 to control transfer of the fluid drug formulation 432 into lumen 103 of hollow wire 102 during the capillary filling procedure as described in FIGS. 4A-7. FIGS. 31A-31B illustrate a portion of lower or second chamber 424 having a portion of a stent 100 lowered to contact a wicking means 3130A, 3130B, respectively. Wicking means 3130A is a sheet or generally flat solid/impervious substrate in contact with a heating element HE, while wicking means 3130B is a porous or open-celled substrate in contact with a heating element HE. To fill stent 100 via capillary action in FIG. 31A, fluid drug formulation 432 is placed on the top surface of impervious wicking means 3130A. Fluid drug formulation 432 spreads out over the top surface of wicking means 3130A, thereby extending to or reaching stent 100 which is also placed on or adjacent to the top surface of wicking means 3130A. To fill stent 100 via capillary action in FIG. 31B, stent 100 is brought into contact with the top surface of porous wicking means 3130B, which is in contact with fluid drug formulation 432 and conveys the fluid drug formulation to the stent. When filling is complete, wicking means 3130A, 3130B are heated via the heating element to alter the surface tension of the wicking means. When wicking means 3130A, 3130B are heated, the surface tension forces between fluid drug formulation 432 and stent 100 are weakened and the fluid drug formulation is prevented from adhering to the interface between wicking means 3130A, 3130B and stent 100. Changes of the temperature of wicking means 3130A, 3130B changes surface tension/affinity properties, and thereby controls transfer of the fluid drug formulation 432 into lumen 103 of hollow wire 102 during the capillary filling procedure.

Figure 32A:
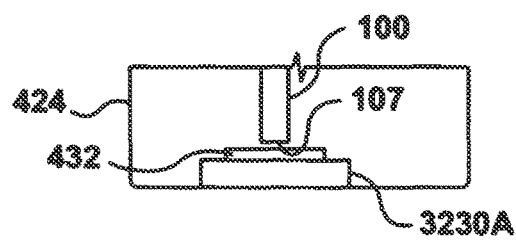
FIGS. 32A-32B illustrate another embodiment of a wicking means, which controls transfer of a fluid drug formulation to a stent during the capillary filling procedure described in FIGS. 4A-7.
Figure 32B:
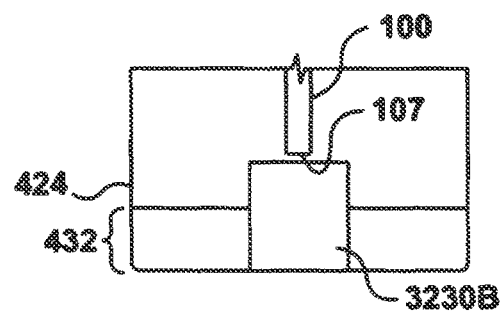

FIGS. 32A-32B illustrate another embodiment of the wicking means in which an intermediate surface or component that is in contact with fluid drug formulation 432 to control transfer of the fluid drug formulation 432 into lumen 103 of hollow wire 102 during the capillary filling procedure as described in FIGS. 4A-7. FIGS. 32A-32B illustrate a portion of lower or second chamber 424 having a portion of a stent 100 lowered to contact a wicking means 3230A, 3230B, respectively. Wicking means 3230A is a sheet or generally flat solid/impervious substrate in contact with a voltage source (not shown), while wicking means 3230B is a porous or open-celled substrate in contact with a voltage (not shown). Wicking means 3230A, 3230B are formed from a polymer material that switches between hydrophilic and hydrophobic based upon applied voltage. To fill stent 100 via capillary action in FIG. 32A, fluid drug formulation 432 is placed on the top surface of impervious wicking means 3230A. Fluid drug formulation 432 spreads out over the top surface of wicking means 3230A, thereby extending to or reaching stent 100 which is also placed on or adjacent to the top surface of wicking means 3230A. To fill stent 100 via capillary action in FIG. 32B, stent 100 is brought into contact with the top surface of porous wicking means 3230B, which is in contact with fluid drug formulation 432 and conveys the fluid drug formulation to the stent. During the filling step, wicking means 3230A, 3230B is hydrophobic to allow fluid drug formulation 432 to fill stent 100 via capillary action. When filling is complete, a voltage or potential is applied to wicking means 3230A, 3230B via the voltage source to change the wicking means to hydrophilic. When the wicking means becomes hydrophilic, the surface tension forces between fluid drug formulation 432 and stent 100 is weakened and the fluid drug formulation is prevented from adhering to the interface between wicking means 3230A, 3230B and stent 100. Suitable polymers for wicking means 3230A, 3230B are described in "Electrically Controlled Hydrophobicity in a Surface Modified Nanoporous Carbon" by Kim et al. (2011) and "Electrowetting of Water and Aqueous Solutions on Poly(ethylene Terephthalate) Insulating Films" by Vallet et al. (1996), each of which is herein incorporated by reference in its entirety.

Figure 33:
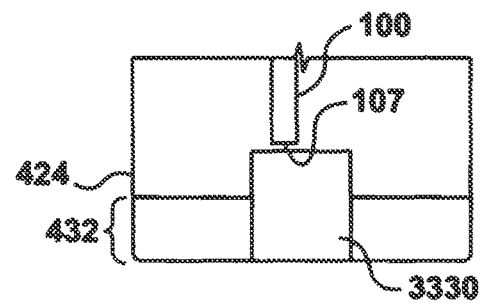
FIG. 33 illustrates another embodiment of a wicking means, which controls transfer of a fluid drug formulation to a stent during the capillary filling procedure described in FIGS. 4A-7.

FIG. 33 is another embodiment of the wicking means as an intermediate surface or component that is in contact with fluid drug formulation 432 to control transfer of the fluid drug formulation 432 into lumen 103 of hollow wire 102 during the capillary filling procedure as described in FIGS. 4A-7. FIG. 33 illustrates a portion of lower or second chamber 424 having a portion of a stent 100 lowered to contact a wicking means 3330. Wicking means 3330 is a porous or open-celled substrate. In an embodiment, wicking means 3330 includes a top layer or polyurethane sheet that has been welded to a sheet of open celled polyethylene foam. A top surface or portion of wicking means 3330 is more hydrophilic than a center or middle portion of wicking means 3330. Wicking means 3330 is in contact with fluid drug formulation 432 and conveys the fluid drug formulation to the stent. To initiate filling, stent 100 is pressed into the less hydrophilic center of wicking means 3330. Since the center portion of wicking means 3330 is less hydrophilic, fluid drug formulation 432 is permitted to fill stent 100 via capillary action. When filling is complete, stent 100 is retracted out of wicking means 3330 and as the stent passes through the top portion, any excess fluid drug formulation 432 which is on an exterior surface of the hollow wire is attracted to the more hydrophilic top portion of wicking means 3330. Thus, during retraction of stents 100, the more hydrophilic top portion of wicking means 3370 may pull or remove excess fluid drug formulation from the exterior surfaces of hollow wires 102 of stents 100.

FIGS. 34-38B illustrate various wicking means embodiments in which the wicking means that minimize the contact area between stent 100 and fluid drug formulation 432 in order to assist in the movement of fluid drug formulation 432 into lumen 103 of hollow wire 102. More particularly, in the embodiments of FIGS. 34-38B, a portion of each stent 100 directly contacts fluid drug formulation 432 but a wicking means is utilized in order to minimize the contact area there between. For illustrative purposes, stents 100 are represented as straight tubular structures in FIGS. 34-38B although it will be understood by one of ordinary skill in the art that stents 100 are a hollow wire shaped into a desired stent pattern as described with reference to FIG. 1. When stents 100 contact fluid drug formulation 432 directly, the surface energy properties of the fluid drug formulation are preferably controlled in order to accurately and predictably fill lumen 103 of hollow wire 102. Without modification of the surface energy properties, the fluid drug formulation may travel up the lumen or central blood flow passageway 113 of stent 100 (see FIG. 1A) and stick to the inner surface or diameter of the stent. It is preferable for fluid drug formulation 432 to have the greatest affinity for lumen 103 of hollow wire 102 rather than on the exterior surfaces of hollow wire 102 so that the maximum amount of exterior surfaces are kept clean, or substantially free of fluid drug formulation 432, during the filling process. One way to decrease the surface tension of fluid drug formulation 432 is to utilize a wicking means that minimizes the contact area between stent 100 and fluid drug formulation 432.

Figure 34:
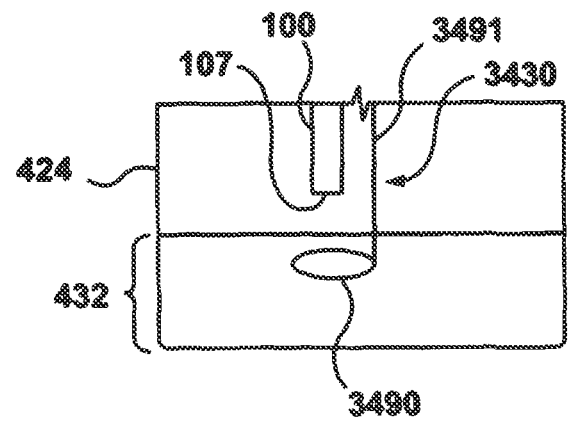
FIG. 34 illustrates another embodiment of a wicking means, which minimizes the contact area between each stent and the fluid drug formulation in order to control transfer of a fluid drug formulation to a stent during the capillary filling procedure described in FIGS. 4A-7.

More particularly, FIG. 34 is an embodiment hereof in which a wicking means 3430 is utilized to reduce the amount of fluid drug formulation 432 exposed to stent 100. FIG. 34 illustrates a portion of lower or second chamber 424 having a portion of a stent 100 lowered to contact (not shown) a wicking means 3430. Although only one stent 100 is shown, it will be understood by one of ordinary skill in the art that wicking means 3430 may accommodate a plurality of stents 100. Wicking means 3430 includes a wire loop 3490 coupled to a wire handle 3491. Stent 100 is placed into second chamber 424 until end 107 of stent 100 is just above but not in contact with the layer of fluid drug formulation 432. Wicking means 3430 is lifted out of fluid drug formulation 432 and brought into contact with end 107 of stent 100. Loop 3490 includes a film of fluid drug formulation 432 similar to a bubble blower loop having a film of bubble solution after the blower loop is lifted out of bubble solution. When brought into contact with the film of fluid drug formulation 432 held within loop 3490, stent 100 breaks the film and fluid drug formulation 432 is transferred to stent 100 via capillary action. Wicking means 3430 transfers a smaller amount of fluid drug formulation 432 to stent 100 and thereby reduces the contact area between stents 100 and fluid drug formulation 432 to control surface energy properties during the filling procedure. Wire loop 3490 may be re-submerged into fluid drug formulation 432 and the filling steps repeated until stent 100 is completely filled.

Figure 35:
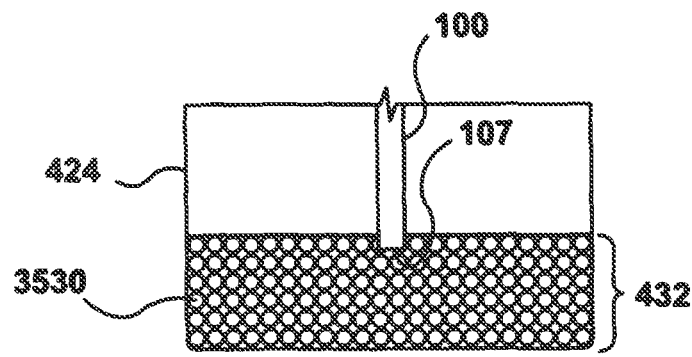
FIG. 35 illustrates another embodiment of a wicking means, which minimizes the contact area between each stent and the fluid drug formulation in order to control transfer of a fluid drug formulation to a stent during the capillary filling procedure described in FIGS. 4A-7.

FIG. 35 is another embodiment for minimizing the contact area between stent 100 and fluid drug formulation 432. FIG. 35 illustrates a portion of lower or second chamber 424 having a portion of a stent 100 lowered to contact a wicking means 3530. Although only one stent 100 is shown, it will be understood by one of ordinary skill in the art that wicking means 3530 may accommodate a plurality of stents 100. Wicking means 3530 is a plurality of beads within the layer of fluid drug formulation 432 contained within second chamber 424. Stent 100 is placed into a layer of beads until end 107 of stent 100 contacts fluid drug formulation 432. The individual size of the beads, as well as the height of the layer of beads, may vary according to application. The beads minimize the contact area between stents 100 and fluid drug formulation 432 to control surface energy properties during the filling procedure. After stents 100 have been filled, stents 100 are retracted through the beads of wicking means 3530. During retraction of stents 100, the beads pull or remove excess fluid drug formulation from the exterior surfaces of hollow wires 102 of stents 100. In FIG. 35, the layer of fluid drug formulation is approximately the same height as the layer of beads. However, in another embodiment (not shown), the layer of beads has a greater height than the layer of fluid drug formulation such that a layer of "dry" beads extend over the "wet" beads that are submersed in the layer of fluid drug formulation. The layer of "dry" beads provides additional cleaning of the exterior surfaces of stents 100 when stents 100 are retracted out of the beads. In an embodiment, the beads of wicking means 3430 may be stirred or shifted during the filling and retracting steps of the process. For example, a magnetic stir stick (not shown) may be used to stir the beads and ensure that the stents are constantly supplied with fluid drug formulation during the filling step. In another example, a piezoelectric crystal (not shown) may be used to vibrate the beads within second chamber 424 to ensure that the stents are constantly supplied with fluid drug formulation during the filling step.

In one embodiment, the beads of wicking means 3530 may be glass beads. Other suitable materials for the beads of wicking means 3530 include ceramic, steel, aluminum, titanium, or stainless steel. Optionally, the beads may be encased in a mesh bag or container (not shown) to ensure that the beads do not stick to stent 100. In another embodiment, the beads may be formed out of a magnetic material. If the magnetic beads stick to stent 100 when stent 100 is retracted out of the wicking means, a magnet (not shown) may be utilized to remove the magnetic beads from stent 100.

FIGS. 36A-37C illustrate another embodiment for minimizing the contact area between stent 100 and fluid drug formulation 432. FIG. 36A illustrates a portion of second chamber 424 having a portion of a stent 100 lowered to contact a wicking means 3630, while FIGS. 37B and 37C illustrate top and side views, respectively, of the wicking means 3630 removed from the chamber and devoid of fluid drug formulation for illustrative purposes. Wicking means 3630 is a generally flat solid plate 3692 having a plurality of reservoirs or grooves 3694 formed on a top surface thereof. Grooves 3694 are channels that are etched onto plate 3692 and function to receive fluid drug formulation. The size and shape of each groove depends upon the size and shape of a stent which is to be placed into contact with the fluid drug formulation within the groove. Although wicking means 3630 is shown with six grooves 3694 for accommodating six stents, it will be understood by one of ordinary skill in the art that wicking means 3630 may include a greater or lesser number of grooves to accommodate the desired number of stents. Plate 3692 is shown as rectangular, but may be any shape that fits within and on a bottom surface of chamber 424. In an embodiment, plate 3692 is glass. Plate 3692 is positioned on the bottom surface of chamber 424, and fluid drug formulation 432 is poured into grooves 3694. Stent 100 is lowered into second chamber 424 until end 107 of each stent 100 contacts fluid drug formulation 432 contained within a respective groove 3694. Since fluid drug formulation 432 is only held within grooves 3694 rather than as a layer on the bottom surface of the chamber, wicking means 3630 minimizes the contact area between stents 100 and fluid drug formulation 432 to control surface energy properties during the filling procedure.

Similar to the embodiment of FIGS. 36A-36C, FIGS. 37A-37C illustrate another embodiment for minimizing the contact area between stent 100 and fluid drug formulation 432. FIG. 37A illustrates a portion of second chamber 424 having a portion of a stent 100 lowered to contact a wicking means 3730, while FIGS. 37B and 37C illustrate top and side views, respectively, of the contact area minimize 3730 removed from the chamber and devoid of fluid drug formulation for illustrative purposes. Wicking means 3730 is a generally flat solid plate 3792 having a plurality of holes or fluid passageways 3794 formed there through. Although wicking means 3730 is shown with six holes 3794 for accommodating six stents, it will be understood by one of ordinary skill in the art that wicking means 3730 may include a greater or lesser number of holes to accommodate the desired number of stents. Plate 3792 is shown as rectangular, but may be any shape that fits within and on a bottom surface of chamber 424. In an embodiment, plate 3792 is stainless steel. Plate 3792 is positioned within chamber 424 on top of a layer of fluid drug formulation 432. Fluid drug formulation 432 seeps through and fills holes 3794 of plate 3792 as shown in FIG. 37A. The size and shape of each hole depends upon the size and shape of a stent which is to be placed into contact with the fluid drug formulation disposed within the hole. To initiate fill, plate 3792 is placed on top of a layer of fluid drug formulation 432 such that fluid drug formulation 432 seeps up into and fills holes 3794 of plate 3792. Stents 100 are then lowered into second chamber 424 until end 107 of each stent 100 contacts the fluid drug formulation 432 disposed within a respective hole 3794. Alternatively, to initiate fill, stents 100 may first be lowered into a position slightly above the layer of fluid drug formulation 432, and plate 3792 may subsequently be lowered into fluid drug formulation 432 with stents 100 passing through holes 3794 of plate 3792. After the plate is placed on top of the layer of fluid drug formulation 432, the fluid drug formulation 432 will seep up or rise into holes 3794 and contact ends 107 of stents 100. Since stents 100 only contact a relatively small amount of fluid drug formulation 432 held within holes 3794, wicking means 3730 minimizes the contact area between stents 100 and fluid drug formulation 432 to control surface energy properties during the filling procedure. After filling is complete, stents 100 and/or plate 3792 may be retracted such that stents 100 are no longer in contact with fluid drug formulation 432.

Figure 38A:
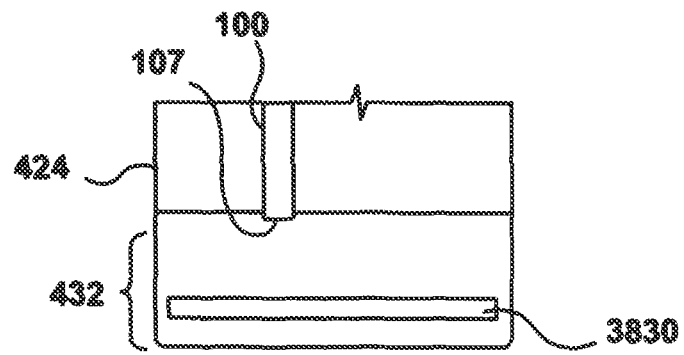
FIGS. 38A-38B illustrate another embodiment of a wicking means, which minimizes the contact area between each stent and the fluid drug formulation in order to control transfer of a fluid drug formulation to a stent during the capillary filling procedure described in FIGS. 4A-7.
Figure 38B:
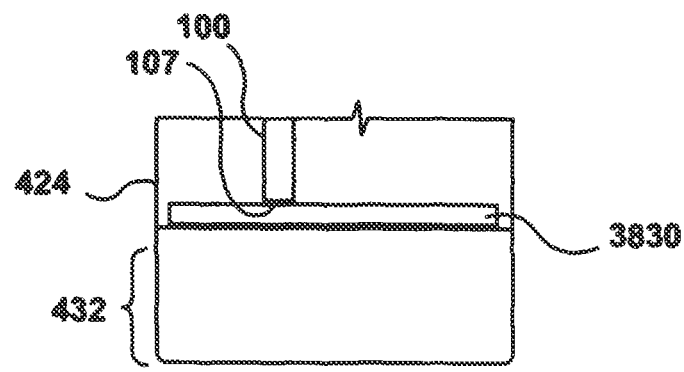

FIGS. 38A-38B illustrate another embodiment for minimizing the contact area between stent 100 and fluid drug formulation 432. FIG. 38A illustrates a portion of lower or second chamber 424 having a portion of a stent 100 lowered to contact (not shown) a wicking means 3830. Although only one stent 100 is shown, it will be understood by one of ordinary skill in the art that wicking means 3830 may accommodate a plurality of stents 100. Wicking means 3830 is a movable plate having an outer diameter or dimension smaller than an inner diameter or dimension of second chamber 424. Prior to and/or during the filling step, the movable plate of wicking means 3830 is positioned within the layer of fluid drug formulation 432, i.e., below the top surface of the layer, as shown in FIG. 38A. To initiate filling, stents 100 are lowered into second chamber 424 until end 107 of stent 100 contacts the layer of fluid drug formulation 432. When it is desired to slow or stop filling, the movable plate of wicking means 3830 is moved up towards stent 100. The movable plate of wicking means 3830 maybe moved via any suitable mechanical or magnetic means. As the movable plate of wicking means 3830 is being moved up, the amount of fluid drug formulation 432 exposed to stent 100 is continually decreased, thereby slowing filling of stent 100. When the movable plate is positioned adjacent to end 107 of stent 100, above the top surface of the layer of fluid drug formulation 432 as shown in FIG. 38B, stent 100 is no longer in contact with the layer of fluid drug formulation 432 and thus stent 100 stops filling.

Although wicking means embodiments described herein may be shown with only one stent 100, it will be understood by one of ordinary skill in the art that any wicking means described herein may accommodate a plurality of stents 100.
Embodiments in which Stents Directly Contact Fluid Drug Formulation without a Wicking Means Although the capillary filling procedure described in FIGS. 4A-7 utilizes a wicking means 430 that is in contact with drug formulation 3932, in another embodiment hereof stent 100 may contact the fluid drug formulation directly without a wicking means. More particularly, FIG. 39 is a schematic illustration of an apparatus 3920 for filling lumen 103 of a stent 100 with a fluid drug formulation 3932 via capillary action without the use of a wicking means. Similar to apparatus 420, apparatus 3920 includes a first or upper chamber 3922 which houses a manifold or stent suspension means 3928 and a reservoir 3931 filled with a liquid or fluid solvent 3933, a second or lower chamber 3924 which houses a fluid drug formulation 3932 that includes therapeutic substance or drug 112, and a valve 3926 extending between upper chamber 3922 and lower chamber 3924. Solvent 3933 within reservoir 3931 is the same solvent as used in fluid drug formulation 3932. A plurality of stents 100 are loaded onto stent suspension means 3928, which holds them in place during the capillary filling procedure and may be any stent suspension means described herein. Prior to the initiation of capillary filling, valve 3926 is closed such that first or upper chamber 3922 and second or lower chamber 3924 are separated and not in fluid communication. A pressure source 3934 and a heat source 3935 are connected to the interior of the upper chamber 3922. Before placing stents 100 into upper chamber 3922, pressure source 3934 is used to purge any residual solvent vapor from the upper chamber. After the purge, stent suspension means 3928 holding stents 100 are placed into upper chamber 3922 and pressure source 3934 is stopped to allow solvent vapor from reservoir 3931 contained solvent 3933 to fill upper chamber 3922. When evaporation has stopped or sufficiently slowed, valve 3926 is opened and first or upper chamber 3922 and second or lower chamber 3924 are exposed to each other and in fluid communication. Both chambers 3922, 3924 are then required to reach or near solvent vapor saturation, or at or near the vapor-liquid equilibrium of solvent 3933, such that little to no net evaporation of the fluid drug formulation is present. In order to reduce the amount of time required for upper and lower chambers 3922, 3924 to reach solvent vapor saturation, upper chamber 3922 may include a fan 3999 to create convection across reservoir 3931 containing a supply of solvent 3933. In addition, any of the methods described above with respect to FIGS. 4A-7 for reducing the amount of time required to reach solvent vapor saturation may be utilized.

Once both chambers 3922, 3924 are at or near solvent vapor saturation, capillary filling may be initiated by moving stents 100 into contact with or submersed into fluid drug formulation 3932. Lumen 103 of hollow wire 102 of stent 100 is filled by surface tension driving fluid drug formulation 3932 through the stent lumen, until the entire length of lumen 103 is filled via capillary action forces. When stents 100 contact fluid drug formulation 3932 directly, the surface energy properties of the fluid drug formulation are preferably controlled in order to accurately and predictably fill lumen 103 of hollow wire 102. As described above with respect to FIGS. 34-38B, without modification of the surface energy properties, the fluid drug formulation may travel up the lumen or central blood flow passageway 113 of stent 100 (see FIG. 1A) and stick to the inner surface or diameter of the stent. In one embodiment, after filling is complete but prior to the retraction or removal of the stents from fluid drug formulation 3932, heat source 3935 may be utilized to raise the temperature of the fluid drug formulation from −50 degrees C. to 60 degrees C. in order to decrease the surface tension thereof.

The stents are filled via capillary action until lumen 103 of hollow wire 102 is filled. During the filling step, chambers 3922, 3924 must be maintained at or near the vapor-liquid equilibrium of solvent 3933 such that evaporation does not precipitate therapeutic substance or drug 112 as fluid drug formulation 3932 fills lumen 103 of hollow wire 102 of stents 100. After lumen 103 is completely filled, stents 100 are retracted or pulled up such that stents 100 are still located within lower chamber 3924 but ends 107 of stents 100 are no longer in contact with fluid drug formulation 3932. The final step of the capillary action filling process includes extracting the solvent or dispersion medium of fluid drug formulation 3932 from within the lumenal space, thereby precipitating the solute, i.e., therapeutic substance or drug 112, within lumen 103 and creating a drug-filled stent 100. More particularly, stents 100 are retracted into upper chamber 3922, which is still at or near vapor-liquid equilibrium of solvent 3933, and valve 3926 is closed such that the chambers 3922, 3924 are no longer in fluid communication. Valve 3926 is closed to isolate fluid drug formulation 3932 from the upper chamber 3922 so that evaporation does not occur from the fluid drug formulation and additional batches of stents may be filled with the same fluid drug formulation without concentration changes. Upper chamber 3922 is then vented to reduce its solvent vapor pressure back to ambient pressure. As the solvent vapor pressure is reduced in the upper chamber, evaporation within lumen 103 of hollow wire 102 is initiated and the solvent of drug fluid formulation 3932 is removed, thereby precipitating its constituents.

When stents 100 directly contact the fluid drug formulation without a wicking means, an additional cleaning step may be utilized after the stent is filled via capillary action in order to remove excess fluid drug formulation from the exterior surfaces of stents 100. If included, the additional cleaning step is preferably performed after the filling step but prior to the solvent evaporation step. Thus, stent 100 may remain in second chamber 3924 of apparatus 3900 during the cleaning step or may be retracted into the upper chamber 3922 of apparatus 3900 during the cleaning step as shown in FIG. 39. A cleaning element 3995 that removes excess fluid drug formulation from the exterior surfaces of hollow wire 102 of stent 100 may be included within first or second chamber 3922, 3924 of apparatus 3900. For example, in one embodiment, cleaning element 3995 is a dry sponge (independent from a sponge that may be utilized as a wicking means) that stents 100 may be dabbed or blotted on to remove excess fluid drug formulation from the exterior surfaces of stent 100. In another embodiment, cleaning element 3995 is a reservoir of dry glass beads (independent from any beads being utilized as a wicking means) that stents 100 may be inserted into to remove excess fluid drug formulation from the exterior surfaces of hollow wire 102 of stent 100. The dry glass beads may be vibrated, i.e., via a piezoelectric crystal, to assist in the cleaning step. In yet another embodiment, cleaning element 3995 is a squeegee that stents 100 may be inserted into to remove excess fluid drug formulation from the exterior surfaces of stent 100. In yet another embodiment, cleaning element 3995 generates movement in order to remove excess fluid drug formulation from the exterior surfaces of stents 100. For example, cleaning element 3995 may generate force by acceleration and/or deceleration to remove excess fluid drug formulation from the exterior surfaces of hollow wire 102 of stent 100. More particularly, stents 100 may be accelerated to spin off excess fluid drug formulation from the exterior surfaces of stents 100. Alternatively or in addition, cleaning element 3995 may be a piezoelectric crystal that generates movement/vibration to removes excess fluid drug formulation from the exterior surfaces of stent 100. A piezoelectric crystal may be incorporated onto the carousel/mandrel of the stent suspension means in the upper chamber of the apparatus.

In addition or as an alternative to a cleaning step, at least a portion of the exterior surface of hollow wire 102 of stent 100 may be masked during the filling procedure to prevent the submersed exterior surface from being exposed to the fluid drug formulation. In one embodiment, a monolayer or coating may be applied over at least a portion of stent 100 to mask or cover the exterior surfaces of hollow wire 102 of stent 100 that are to be exposed to a fluid drug formulation, while leaving the drug delivery side ports or openings 104 of stent 100 open so that the fluid drug formulation can fill the lumen of the hollow wire. The monolayer or coating having any excess fluid drug formulation adhered thereto may be removed after the filling process is complete. In an embodiment in which the fluid drug formulation is hydrophilic, the coating is preferably hydrophobic. As the lumenal space of the wire fills, the hydrophilic fluid drug formulation does not stick to the coating or any exposed exterior surfaces of the hollow wire of the stent due to the hydrophobic property of the coating. In another embodiment, as opposed to a coating, a sleeve that slides over hollow wire 102 may be utilized to mask or cover the exterior surfaces of hollow wire 102 of stent 100 that are to be exposed to a fluid drug formulation.

Although the cleaning and/or masking embodiments described above have been discussed in conjunction with embodiments in which stents directly contacts a fluid drug formulation without a wicking means, such cleaning and/or masking embodiments described herein may be utilized with any embodiment described herein, including those which utilize a wicking means. In addition, although the cleaning embodiments described above occur between the filling and drying/evaporation steps of the process, additional and/or alternative cleaning steps may be applied after the drying/evaporation step of the process. For example, U.S. Patent Application Publication 2012/0070562 entitled "Apparatus and Methods for Filling a Drug Eluting Medical Device" to Avelar et al., herein incorporated by reference in its entirety, describes several stent cleaning methods that may be utilized herewith. Any combination of the aforementioned cleaning methods can be employed to clean the stent. The selection of cleaning method(s) may be governed by factors such as the drug formulation components and the degree of drug residue after the filling process via capillary action is complete.

Other Applications of Capillary Filling Process

In addition to filling stents formed via a hollow wire for drug delivery, embodiments of the capillary action filling process described above may be applied to other structures. For example, structures having a lumen of a sufficiently small size, such as lumen 103 of hollow wire 102 of stent 100, can be impregnated with any fluid formulation using a capillary action filling process described above. Since only one side opening 104 of the stent is required to be exposed to the fluid formulation, fill weight variation and waste is reduced. In addition to structures having a sufficiently small lumen, structures formed from a porous material, or having a porous material on at least an exterior surface thereof, may be impregnated with any fluid formulation using a capillary action filling process described above. For example, an implantable polyurethane sponge may be impregnated with a fluid drug formulation similar to those described herein for in situ delivery. Other examples include impregnating a wound dressing with antibiotic, impregnating a porous bioabsorbable disc that will be implanted subcutaneously with a fluid drug formulation that suppresses appetite, impregnating a porous bioabsorbable sphere that is to be implanted into a muscle with a fluid drug formulation that encourages muscle growth after atrophy, and impregnating a bioabsorbable stent formed from a porous material with a fluid drug formulation similar to those described herein. Various deformable porous materials that may be impregnated with any fluid formulation using a capillary action filling process described above include porous polymers and hydrogels such as polyurethanes, PEG, PLGA, PLA, PGA, and PE, cotton, silk, TELFA, and cellulose.

Rigid materials, such as metals, ceramics, and rigid polymers, are often utilized as implants and it may be desired to impregnate a rigid material with a fluid drug formulation. Exemplary rigid materials include aluminum, stainless steel, silver, gold, molybdenum, tungsten, tantalum, bronze, ceramics such as borosilicate, hydroxyapatitie, silicon nitride, zirconium dioxide, and polymers such as PET, Polypropylene, HDPE, PVC, polyamides, and fluoropolymers. In order to become porous, rigid materials may undergo processing steps, such as dry etch, a wet or acid etch, application of sintered metal or ceramic powder, application of a metal mesh, or injection of inert gas during liquid metal or polymer solidification. After becoming porous, the rigid materials may then be impregnated with any fluid formulation using a capillary action filling process described above. For example, a hip implant formed from a rigid porous material may be impregnated with a steroid to reduce inflammation after implantation or a spinal screw/plate/rod may be impregnated with an API that encourages bone growth and/or healing.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of filling a fluid drug formulation within a lumenal space of a hollow wire having a plurality of side openings along a length thereof that forms a medical device, the method comprising the steps of:
    placing the medical device formed from a hollow wire having a plurality of side openings within a chamber, wherein the chamber houses a fluid drug formulation and a plurality of beads that are in contact with the fluid drug formulation;
    placing a portion of the medical device into contact with the plurality of beads such that at least one of the plurality of side openings is in contact with the plurality of beads; and
    maintaining contact between the plurality of beads and the portion of the medical device placed into contact with the plurality of beads until a lumenal space defined by the hollow wire is filled with the fluid drug formulation via capillary action through the at least one of the plurality of side openings in contact with the plurality of beads.

2. The method of claim 1, further comprising the steps of:
    retracting the medical device such that the portion of the medical device is no longer in contact with the plurality of beads.

3. The method of claim 2, wherein the step of retracting the medical device such that the portion of the medical device is no longer in contact with the plurality of heads removes excess fluid drug formulation from an exterior surface of the hollow wire during the step of retracting the medical device.

4. The method of claim 1, wherein the plurality of beads comprises at least one of glass beads, ceramic beads, steel beads, aluminum beads, titanium beads, stainless steel beads or polymeric beads.

5. The method of claim 1 further comprising applying a voltage or potential to the plurality of beads causing the plurality of beads to become hydrophilic.

6. The method of claim 5, wherein after the hollow wire is filled with the fluid drug formulation, the method further comprises applying the voltage or potential to the plurality of beads causing the plurality of beads to become hydrophobic.

7. The method of claim 1 further comprising vibrating the plurality of beads.

8. The method of claim 1 further comprising stirring the plurality of beads.

9. A method of filling a fluid drug formulation within a lumenal space of a hollow wire having a plurality of side openings along a length thereof that forms a medical device, the method comprising the steps of:
    placing a medical device formed from a hollow wire having a plurality of side openings within a chamber, wherein the chamber houses a plurality of beads disposed within a fluid drug formulation and wherein the plurality of beads has first and second layers of beads such that the first layer of beads extends over the second layer of beads and the second layer of beads is submersed in the fluid drug formulation;
    placing a portion of the medical device into contact with the second layer of beads such that at least one of the plurality of side openings is in contact with the fluid drug formulation;
    maintaining contact between the fluid drug formulation and the portion of the medical device until a lumenal space defined by the hollow wire is filled with the fluid drug formulation via capillary action through the at least one of the plurality of side openings in contact with the fluid drug formulation;
    retracting the medical device such that the portion of the medical device is no longer in contact with the fluid drug formulation; and
    removing fluid drug formulation from an exterior surface of the hollow wire by further retracting the medical device such that the portion of the medical device which was in contact with the fluid drug formulation passes through the first layer of beads.

10. The method of claim 9, further comprising the step of:
    increasing the temperature of the fluid drug formulation after the step of maintaining contact between the fluid drug formulation and the portion of the medical device until a lumenal space defined by the hollow wire is filled with the fluid drug formulation via capillary action but prior to the step of retracting the medical device.

11. The method of claim 9, further comprising the step of:
covering at least a portion of an exterior surface of the hollow wire with a coating prior to the step of placing an end of the medical device into contact with the fluid drug formulation.

12. The method of claim 9, wherein the plurality of beads comprises at least one of glass beads, ceramic beads, steel beads, aluminum beads, titanium beads, stainless steel beads or polymeric beads.

13. The method of claim 9 further comprising applying a voltage or potential to the plurality of beads causing the plurality of beads to become hydrophilic.

14. The method of claim 9, wherein after the hollow wire is filled with the fluid drug formulation, the method further comprises applying a voltage or potential to the plurality of beads causing the plurality of beads to become hydrophobic.

15. The method of claim 9 further comprising vibrating the plurality of beads.

16. The method of claim 9 further comprising stirring the plurality of beads.

* * * * *